US012582669B2

(12) United States Patent
Kataoka et al.

(10) Patent No.: US 12,582,669 B2
(45) Date of Patent: Mar. 24, 2026

(54) COMPOSITION CONTROLLING PHARMACOKINETICS IN THE BODY

(71) Applicant: KAWASAKI INSTITUTE OF INDUSTRIAL PROMOTION, Kawasaki (JP)

(72) Inventors: Kazunori Kataoka, Kanagawa (JP); Shigehito Osawa, Kanagawa (JP); Satoshi Uchida, Kanagawa (JP); Kotaro Hayashi, Kanagawa (JP); Anjaneyulu Dirisala, Kanagawa (JP); Kazuko Toh, Kanagawa (JP)

(73) Assignee: KAWASAKI INSTITUTE OF INDUSTRIAL PROMOTION, Kawasaki (JP)

( * ) Notice: Subject to any disclaimer, the term of this patent is extended or adjusted under 35 U.S.C. 154(b) by 0 days.

(21) Appl. No.: 18/594,618

(22) Filed: Mar. 4, 2024

(65) Prior Publication Data

US 2024/0207306 A1 Jun. 27, 2024

Related U.S. Application Data

(62) Division of application No. 16/980,063, filed as application No. PCT/JP2019/009919 on Mar. 12, 2019, now Pat. No. 11,957,708.

(30) Foreign Application Priority Data

Mar. 12, 2018 (JP) ................................ 2018-043880

(51) Int. Cl.
*A61K 31/74* (2006.01)
*A61K 31/25* (2006.01)
*A61K 47/00* (2006.01)

(52) U.S. Cl.
CPC .............. *A61K 31/74* (2013.01); *A61K 31/25* (2013.01); *A61K 47/00* (2013.01)

(58) Field of Classification Search
CPC ......... A61K 31/74; A61K 31/25; A61K 47/00
See application file for complete search history.

(56) References Cited

U.S. PATENT DOCUMENTS

| | | | |
|---|---|---|---|
| 8,153,110 B2 | 4/2012 | Kataoka | |
| 8,431,545 B2 | 4/2013 | Kataoka | |
| 8,592,385 B2 | 11/2013 | Kataoka | |
| 9,051,354 B2 | 6/2015 | Kataoka | |
| 9,808,480 B2 | 11/2017 | Kataoka | |
| 10,232,054 B2 | 3/2019 | Kataoka | |
| 10,322,092 B2 | 6/2019 | Kataoka | |
| 10,668,169 B2 | 6/2020 | Kataoka | |
| 11,020,418 B2 | 6/2021 | Kataoka | |
| 11,096,991 B2 | 8/2021 | Kataoka | |
| 2009/0324535 A1 | 12/2009 | Boyd | |
| 2012/0177594 A1 | 7/2012 | Kataoka | |
| 2013/0109743 A1 | 5/2013 | Kataoka et al. | |
| 2015/0080454 A1* | 3/2015 | Kataoka ............. | A61K 47/6455 514/44 A |
| 2016/0287714 A1 | 10/2016 | Kataoka et al. | |
| 2018/0042955 A1 | 2/2018 | Kataoka et al. | |
| 2018/0140680 A1 | 5/2018 | Kataoka et al. | |
| 2018/0289835 A1 | 10/2018 | Kataoka et al. | |
| 2018/0334674 A1 | 11/2018 | Kondo et al. | |
| 2021/0260207 A1 | 8/2021 | Itaka et al. | |
| 2021/0346290 A1 | 11/2021 | Anraku et al. | |

FOREIGN PATENT DOCUMENTS

| | | |
|---|---|---|
| CN | 102727907 A | 10/2012 |
| CN | 102971002 A | 3/2013 |
| CN | 105899192 A | 8/2016 |
| EP | 2 842 546 A1 | 3/2015 |
| JP | 6-198201 B1 | 7/1994 |
| JP | 2017-105802 A | 6/2017 |
| WO | WO 2006/123631 A1 | 11/2006 |
| WO | WO 2013/162041 A1 | 10/2013 |
| WO | WO 2016/178431 A1 | 11/2016 |
| WO | WO 2016/186204 A1 | 11/2016 |
| WO | WO 2018/038155 A1 | 3/2018 |

OTHER PUBLICATIONS

International Search Report issued on Jun. 18, 2019 in PCT/JP2019/009919 filed on Mar. 12, 2019,2 pages.
Osawa, S. et al., “Polyplex Micelles with Double-Protective Compartments of Hydrophilic Shell and Thermoswitchable Palisade of Poly(oxazoline)-Based Block Copolymers for Promoted Gene Transfection,” Biomacromolecules, vol. 17, No. 1, 2016, pp. 354-361.
Minchin, R. F. et al., “Polyinosinic Acid and Polycationic Liposomes Attenuate the Hepatic Clearance of Circulating Plasmid DNA,” The Journal of Pharmacology and Experimental Therapeutics, vol. 296, No. 3, 2001, pp. 1006-1012.
Zheng, M. et al., “Enhancing in vivo circulation and siRNA delivery with biodegradable polyethylenimine-graft-polycaprolactone-block-poly(ethylene glycol) copolymers,” Biomaterials, vol. 33, No. 27, 2012, pp. 6551-6558.
Extended European Search Report issued Nov. 4, 2021 in European Patent Application No. 19768480.6, 7 pages.
Combined Chinese Office Action and Search Report issued Mar. 22, 2023, in corresponding Chinese Patent Application No. 201980018952.7 (with English Translation of Category of Cited Documents), 9 pages.

* cited by examiner

*Primary Examiner* — Michael P Cohen
(74) *Attorney, Agent, or Firm* — Oblon, McClelland, Maier & Neustadt, L.L.P.

(57) ABSTRACT

The present invention provides a composition that controls pharmacokinetics. Specifically, the present invention provides: a composition for controlling pharmacokinetics, the composition containing a polyvalent cation as an active ingredient; and a method for controlling pharmacokinetics using the polyvalent cation.

28 Claims, 12 Drawing Sheets

| | Micelle-only administration group | Polyvalent cation administration group |
| --- | --- | --- |
| Micelles | + | + |
| Polyvalent cations | — | + |

Spleen

Heart

Polyvalent cation non-administration group

Polyvalent cation prior administration group

COMPOSITION CONTROLLING PHARMACOKINETICS IN THE BODY

The present application is divisional of U.S. application Ser. No. 16/980,063, filed Sep. 11, 2020, which is the National Stage of International Application no. PCT/JP2019/009919, filed Mar. 12, 2019, which claims priority to Japanese Patent Application No. 2018-043880, filed Mar. 12, 2018. The contents of these applications are incorporated herein by reference in their entirety.

TECHNICAL FIELD

The present invention relates to a composition that controls pharmacokinetics in the body (such as a composition for changing distribution of a drug, suppressing metabolism of the drug or suppressing excretion of the drug), particularly, an inhibitor of clearance of a drug (such as a pharmaceutically active ingredient and a carrier for drug delivery) from blood by the liver sinusoidal endothelial cells. The present invention further relates to an inhibitor of clearance of a drug from blood by the kidneys. The present invention further relates to a composition for increasing the amount of drug to be delivered to the spleen.

BACKGROUND ART

Pharmacokinetics in the body has great significance in developing pharmaceutical products. For example, the concentration of the drug in blood is, of course, important for exerting the effects of pharmaceutical products. The concentration of the drug in blood is determined by four processes: absorption, distribution, metabolism, and excretion of the drug. In particular, metabolism and excretion (clearance) of the drug are important determinants of the concentration of the drug in blood.

Meanwhile, a ternary copolymer consisting of a hydrophilic block—a temperature-responsive block—a polycationic block has been developed as a technique for enhancing the stability of plasmid DNA in blood (Non Patent Literature 1). This ternary copolymer forms micelles when mixed with plasmid DNA at a low temperature. In this micelle, the plasmid DNA forms a complex together with the polycationic block of the ternary copolymer. Thereafter, the temperature-responsive block changes from hydrophilic to hydrophobic with an increase in temperature, thereby forming a hydrophobic interlayer covering the plasmid DNA, and the interlayer is used as a protective layer of DNA. However, the micelle formulation technique with greatly improved stability of mRNA in blood has not been known yet. A method of forming a copolymer of a hydrophilic segment and a cationic segment together with nucleic acids into a complex so as to neutralize the electric charge is disclosed (Patent Literature 1).

CITATION LIST

Patent Literature

Patent Literature 1: International Publication No. WO 2013/162041

Non Patent Literature

Non Patent Literature 1: Osawa S. et al., Biomacromolecule, 17 (1): 354-361, 2016

SUMMARY OF INVENTION

The present invention provides a composition that controls pharmacokinetics (such as a composition for changing the distribution of a drug, suppressing the metabolism of the drug or suppressing the excretion of the drug), particularly, an inhibitor of the ability of the liver sinusoidal endothelial cells to excrete a drug (such as a pharmaceutically active ingredient and a carrier for drug delivery). The present invention further provides an inhibitor of the ability of the kidneys to excrete a drug from blood.

The inventors have found that polyvalent cations (especially, polyvalent cations modified with polyethylene glycol to enhance their biocompatibility) are localized on the inner vascular surface of the liver sinusoidal endothelial cells and the inner vascular surface of the vascular endothelium of the kidneys and reduce the ability to excrete a drug from the blood. The inventors have further found that polyvalent cations increase the amount of the drug to be delivered to various organs including the spleen or various tissues. The present invention is based on such findings.

That is, the present invention provides the following aspects.

(1A) A composition for use in controlling pharmacokinetics in the body, comprising a polyvalent cation as an active ingredient (where the polyvalent cation may be a cationic polymer).

(2A) The composition according to (1A) above, wherein the polyvalent cation is in the form of a conjugate with a hydrophilic polymer block.

(3A) The composition according to (1A) above, wherein the polyvalent cation is a cationic polymer having two or more hydrophilic polymer chains.

(4A) The composition according to (2A) above, wherein the polyvalent cation is a block copolymer of a cationic polymer block and a branched polyethylene glycol.

(5A) The composition according to any one of (1A) to (4A) above, wherein the control of pharmacokinetics is to control clearance from blood.

(6A) The composition according to any one of (1A) to (5A) above, wherein the control of pharmacokinetics is to reduce the ability of the liver sinusoidal endothelial cells to excrete the drug from blood.

(7A) The composition according to any one of (1A) to (5A) above, wherein the control of pharmacokinetics is to reduce the ability of the kidneys to excrete the drug from blood.

(8A) The composition according to any one of (1A) to (6A) above, wherein the control of pharmacokinetics is to increase an amount to be delivered to a target organ or tissue.

(9A) The composition according to any one of (1A) to (6A) above, wherein the control of pharmacokinetics is to increase an amount to be delivered to the spleen.

(10A) The composition according to any one of (1A) to (4A) above, wherein the control of pharmacokinetics is to increase retention of the drug in blood.

(11A) The composition according to any one of (1A) to (10A) above, which is administered prior to the drug whose kinetics are to be controlled.

(12A) The composition according to any one of (1A) to (10A) above, which is administered simultaneously with the drug whose kinetics are to be controlled.

(13A) The composition according to any one of the aforementioned (1A) to (10A) above, which is administered after the drug whose kinetics are to be controlled (provided that the administration is performed while the drug remains in blood).

(14A) The composition according to any one of (1A) to (13A) above, wherein the polyvalent cation is in a free form or administered in a free form.

(15A) The composition according to any one of (1A) to (14A) above, wherein the drug whose kinetics are to be controlled is encapsulated in a carrier for drug delivery.

(16A) A method for controlling pharmacokinetics, comprising using the composition according to any one of (1A) to (15A).

The present invention further provides the following aspects.

(1B) A composition for use in controlling pharmacokinetics in the body, comprising a cationic polymer as an active ingredient.

(2B) The composition according to (1B) above, wherein the cationic polymer is in the form of a conjugate (for example, a copolymer) with a hydrophilic polymer block.

(3B) The composition according to (1B) above, wherein the cationic polymer is a cationic polymer having two or more hydrophilic polymer chains.

(4B) The composition according to (2B) above, wherein the cationic polymer is a block copolymer of a cationic polymer block and a branched polyethylene glycol.

(5B) The composition according to any one of (1B) to (4B) above, wherein the control of pharmacokinetics is to control clearance from blood.

(6B) The composition according to any one of (1B) to (5B) above, wherein the control of pharmacokinetics is to reduce the ability of the liver sinusoidal endothelial cells to excrete the drug from blood.

(7B) The composition according to any one of (1B) to (5B) above, wherein the control of pharmacokinetics is to reduce the ability of the kidneys to excrete the drug from blood.

(8B) The composition according to any one of (1B) to (6B) above, wherein the control of pharmacokinetics is to increase an amount to be delivered to a target organ or tissue.

(9B) The composition according to any one of (1B) to (6B) above, wherein the control of pharmacokinetics is to increase an amount to be delivered to the spleen.

(10B) The composition according to any one of (1B) to (4B) above, wherein the control of pharmacokinetics is to increase retention of the drug in blood.

(11B) The composition according to any one of (1B) to (10B) above, which is administered prior to the drug whose kinetics are to be controlled.

(12B) The composition according to any one of (1B) to (10B) above, which is administered simultaneously with the drug whose kinetics are to be controlled.

(13B) The composition according to any one of (1B) to (10B) above, which is administered after the drug whose kinetics are to be controlled (provided that the administration is performed while the drug remains in blood).

(14B) The composition according to any one of (1B) to (13B) above, wherein the cationic polymer is in a free form or administered in a free form.

(15B) The composition according to any one of (1B) to (14B) above, wherein the drug whose kinetics are to be controlled is encapsulated in a carrier for drug delivery.

(16B) A method for controlling pharmacokinetics, comprising using the composition according to any one of (1B) to (15B).

DESCRIPTION OF EMBODIMENTS

Figure 1:
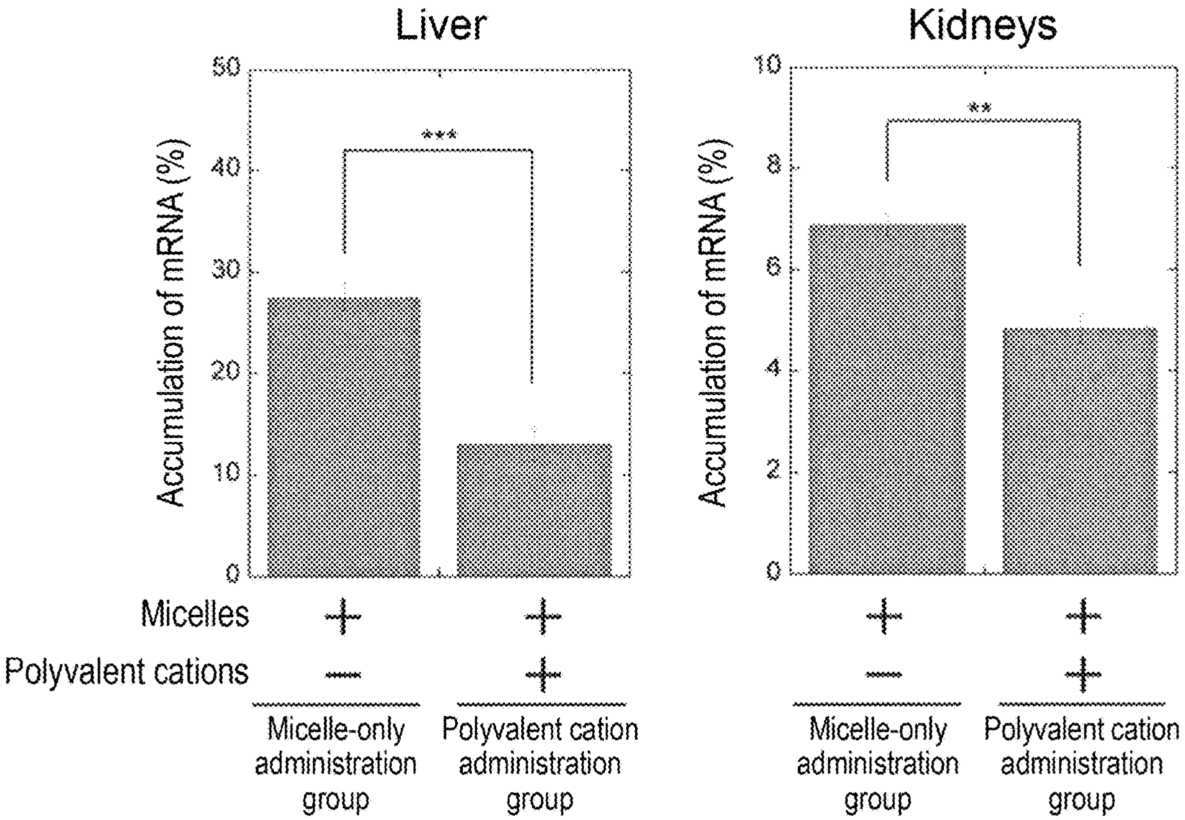
FIG. 1 includes graphs showing the effects of a cationic polymer on accumulation of a carrier (ion complex) in the liver and kidney.

In this description, the "subject" is a mammal including a human. The subject may be a healthy subject or may be a subject suffering from some disease. The subject can be a mammal such as a human, particularly, a mammal such as a human for which administration of the micelles of the present invention is beneficial.

In this description, the term "for drug delivery" means being biocompatible and capable of encapsulating a drug in a carrier. In this description, the term "for drug delivery" may refer to an application for prolonging the time for which a drug remains in blood as compared with the time for which a naked drug remains in blood or an application for improving the amount of a drug to be delivered to a predetermined tissue.

In this description, the term "carrier" refers to fine particles or hollow fine particles capable of encapsulating a substance. The carrier preferably has a biocompatible outer shell or modification. The carrier is not specifically limited, but examples thereof include liposomes and micelles, particularly, liposomes composed of phospholipids, or the like.

In this description, the term "micelles" means a carrier formed by assembly of molecules such as a polymer. Examples of the micelles include micelles formed by amphipathic molecules such as surfactants and micelles formed by polyion complexes (PIC micelles). The micelles preferably have an outer surface modified with an uncharged hydrophilic chain, from the viewpoint of the improvement of the bioavailability.

In this description, the term "average molecular weight" means a number-average molecular weight, unless otherwise specified.

In this description, the term "polymerization degree" means the number of monomer units in the polymer, and the term "average polymerization degree" means the number-average polymerization degree, unless otherwise specified.

In this description, the terms "cationic block" and the "cationic polymer" respectively mean a polymer block and a polymer that are cationic as a whole and obtained by polymerizing monomer units containing cationic monomers. Examples of the cationic polymer include homocationic polymers and polymers in which a homocationic polymer is linked to an uncharged hydrophilic chain. When a cationic polymer forms a block copolymer together with another polymer, the cationic polymer portion may be referred to as a cationic block. In this description, the cationic polymer is a pharmaceutically acceptable cationic polymer. In this description, the term "polyvalent cation" refers to a molecule having a plurality of groups with cationic properties within the molecule, among cationic molecules. In this description, the term "polyvalent cation" can have cationic properties as a whole molecule in blood environment. Examples of the polyvalent cation include molecules that are cationic in the blood environment such as cationic polymers and cationic dendrimers. The polyvalent cation is biocompatible. In this description, the term "dendrimer" refers to a molecule having branches in a plurality of stages from one core atom.

In this description, the term "hydrophilic block" means a polymer chain that is soluble in an aqueous medium and may be a hydrophilic polymer block. In the present invention, the uncharged hydrophilic chain is a pharmaceutically acceptable uncharged hydrophilic chain. Examples of such a hydrophilic chain include polyethylene glycol (PEG) and poly(2-ethyl-2-oxazoline). The uncharged hydrophilic chain may have polar atoms, as long as the electric charge is neutralized both locally and overall. The hydrophilic block may or may not be branched. In the case where the hydrophilic block is branched, the number of branch points can be one or more.

In this description, the terms "temperature-responsive block" and the "temperature-responsive polymer" respectively mean a polymer block and a polymer capable of changing from hydrophilic to hydrophobic, depending on the temperature. There are various known substances that change from hydrophilic to hydrophobic depending on the temperature, and examples thereof include poly(N-isopropyl acrylamide), poly(2-n-propyl-2-oxazoline), and poly(2-isopropyl-2-oxazoline). The temperature-responsive polymer has a lower critical solution temperature (LCST) and is hydrophilic below the LCST and hydrophobic at the LCST or higher. The temperature-responsive polymer comprises a temperature-responsive block. In an embodiment, the temperature-responsive polymer comprises a temperature-responsive block and a hydrophilic block. In an embodiment, the temperature-responsive polymer does not include a cationic block. The temperature-responsive polymer may consist essentially of the temperature-responsive block or may consist of the temperature-responsive block. The lower critical solution temperature (LCST) can be preferably 4° C. or more and 40° C. or less, particularly, can be lower than the body temperature of the subject such as a human.

In this description, the term "ternary copolymer" or "triblock copolymer" means a block copolymer containing three different polymer blocks. Each block may be linked via a linker or a spacer. In the case where the ternary copolymer contains three different blocks, A, B, and C in this order, it can be expressed as "A-B-C". The symbol "-" can be a bond, or a linker or a spacer. The ternary copolymer may contain other different polymer blocks, as long as it contains three different polymer blocks. The ternary copolymer may consist essentially of three different polymer blocks "A-B-C" or consist of "A-B-C".

In this description, the term "outer shell" means a protective layer encapsulating RNA. The outer shell does not necessarily mean to exist as the outermost shell. In this description, the term "protective layer" can protect RNA from degradation due to degrading enzymes such as RNase as compared with the absence of the protective layer.

In this description, the term "comprise" is used in the sense of including "consist of" and "essentially consist of". The term "comprise" means that components other than target components may be contained, and the term "consist of" means that components other than target components are not contained. In this description, the term "consist essentially of" means that components other than target components are not contained in an aspect exerting a particular function (such as an aspect in which the effects of the invention are completely lost).

In this description, the phrase "separately administering A and B" or similar expressions are used in the meaning including administering A and B temporally separately, and administering each of A and B simultaneously without mixing.

In this description, the term "clearance" refers to metabolism and excretion of a drug. For example, the clearance can be reduction of the drug by metabolism or reduction of the drug by excretion from blood. It is known that the clearance reduces retention of the drug in blood.

In this description, the term "target organ or tissue" refers to an organ or tissue to which the drug to be administered is intended to be delivered. The target organ or tissue may differ depending on the type of the drug to be administered and the type of the patient subject to the administration. The term "target organ or tissue" does not mean that the drug is delivered only to the organ or tissue but means that the drug may be delivered to organs or tissues other than the organ or tissue, as long as the drug is delivered to the target organ or tissue. The drug delivery to the "target organ or tissue" is preferably selectively performed to the target organ or tissue. Here, the term "selectively" means that the drug is accumulated more in the target organ or tissue than in the other organs or tissues.

As shown in Examples below, when polyvalent cations were administered to the blood, the polyvalent cations are accumulated on the luminal inner wall of the liver sinusoidal endothelial cells and the kidney vascular endothelial cells, to cover the vascular inner wall. Further, as a result of this, the polyvalent cations reduced clearance of the drug by the liver sinusoidal endothelial cells and the kidney vascular endothelial cells to improve retention of the drug in blood. Therefore, according to the present invention, the polyvalent cations typified by a cationic polymer can be used to control pharmacokinetics in the body.

Further, according to the present invention, a cationic polymer can be used to control the pharmacokinetics in the body.

Here, the control of pharmacokinetics is to improve or change the pharmacokinetics. Examples of the control of pharmacokinetics include controlling clearance. More specifically, examples of the control of pharmacokinetics include reducing the ability of the liver sinusoidal endothelial cells to excrete the drug from blood. Examples of the control of pharmacokinetics also include reducing the ability of the kidneys to excrete the drug from blood. Examples of the control of pharmacokinetics further include increasing the amount to be delivered to the target organ. Examples of the control of pharmacokinetics still further include increasing the amount of drug to be delivered to the spleen. Examples of the control of pharmacokinetics still further include enhancing retention of the drug in blood.

In this way, in the present invention, use of polyvalent cations such as a cationic polymer can suppress metabolism of the drug in blood by the liver sinusoidal endothelial cells or excretion therethrough, suppress metabolism or excretion by the kidneys, enhance retention of the drug in blood, and/or improve the amount of the drug to be delivered to the target organ or tissue (e.g. organs or tissues such as the brain, lungs, heart, and spleen, and tumors). That is, according to the present invention, polyvalent cations such as a cationic polymer control kinetics in the body of other pharmaceutically active ingredients (drugs) to be administered simultaneously or separately. Therefore, according to the present invention, the polyvalent cations such as a cationic polymer are not necessarily pharmaceutically active ingredients. Further, the polyvalent cations such as a cationic polymer do not necessarily form a complex together with pharmaceutically active ingredients (that is, it may be in a free form).

The polyvalent cations may be modified with a hydrophilic polymer, from the viewpoint of improving the bioavailability of the cations themselves.

The cationic polymer may be, for example, in the form of a copolymer of a cationic block and a hydrophilic polymer block, from the viewpoint of improving the bioavailability of the polymer itself.

It can be expected that this improves the bioavailability of the cationic polymer and increases the effect of reducing the ability of the liver sinusoidal endothelial cells to excrete the drug from blood or the effect of reducing the ability of the kidneys to excrete the drug from blood.

An uncharged hydrophilic polymer block, for example, can be used as the hydrophilic polymer block. The uncharged hydrophilic polymer block is a pharmaceutically acceptable polymer. The polymer that may be preferably used is not specifically limited, but examples thereof include polyalkylene glycol, poly(2-oxazoline), polysaccharide, polyvinyl alcohol, polyvinylpyrrolidone, polyacrylamide, polymethacrylamide, polyacrylic acid ester, polymethacrylic acid ester, and poly(2-metacloyloxyethyl phosphorylcholine). As the uncharged hydrophilic polymer, polyalkylene glycol and poly(2-oxazoline) can be preferably used, and polyalkylene glycol can be particularly preferably used. As the polyalkylene glycol, polyethylene glycol (PEG) can be preferably used.

In such a copolymer containing a cationic polymer portion and a PEG portion, the PEG portion can have an average molecular weight, for example, of 10 kD or more, 15 kD or more, 20 kD or more, 30 kD or more, or 40 kD or more (and 80 kD or less, 70 kD or less, 60 kD or less, or 50 kD or less), preferably 20 kD or more, more preferably 30 kD or more. In this copolymer containing a cationic polymer portion and a PEG portion, the cationic polymer can have an average polymerization degree of 15 or more, 20 or more, 30 or more, or 40 or more (and 80 or less, 70 or less, 60 or less, or 50 or less, for example). From the viewpoint of increasing the bulk of the PEG portion, the PEG portion can be a single-stranded PEG with a large average molecular weight, such as 40 kD or more, 50 kD or more, 60 kD or more, or 70 kD or more (and 80 kD or less, 70 kD or less, 60 kD or less, or 50 kD or less, for example) or can be branched PEG having a plurality of PEG chains of 10 kD or more, 15 kD or more, 20 kD or more, 30 kD or more, or 40 kD or more (and 80 kD or less, 70 kD or less, 60 kD or less, or 50 kD or less, for example). From the viewpoint of increasing the bulk of the PEG portion, such branched PEG can be preferably used.

In an aspect, in the copolymer containing a cationic polymer portion and a PEG portion, the PEG portion can be a branched PEG having a plurality of PEG chains of 10 kD or more, 15 kD or more, 20 kD or more, 30 kD or more, or 40 kD or more, and the cationic polymer portion can have an average polymerization degree of 15 or more, 20 or more, 30 or more, or 40 or more. In this specific aspect, in the copolymer containing a cationic polymer and PEG, the PEG portion can be a branched PEG having a plurality of PEG chains of 20 kD or more, 30 kD or more, or 40 kD or more, and the cationic polymer portion can have an average polymerization degree of 20 or more, 30 or more, or 40 or more.

In an aspect, in the copolymer containing a cationic polymer portion and a PEG portion, the PEG portion can be a single-stranded PEG of 40 kD or more, and the cationic polymer portion can have an average polymerization degree of 15 or more, 20 or more, 30 or more, 40 or more, 50 or more, 60 or more, or 70 or more (and 80 or less, 70 or less, 60 or less, or 50 or less, for example; particularly in the case of a single-stranded PEG, the larger the average molecular weight is, the greater the effect of improving the retention in blood is).

In a specific aspect, the cationic polymer block can have an average polymerization degree of 15 to 30, the cationic polymer block can be linked to the branched PEG, and the branched PEG can have a total average molecular weight of PEG portions of 40 kD to 100 kD, 50 kD to 90 kD, or 60 kD to 80 kD. Further, for example, the branched PEG can be branched at one site, and the PEG chains extending from the branching site can each independently have an average molecular weight, for example, of 20 kD to 60 kD, 25 kD to 50 kD, or 30 kD to 40 kD. According to the present invention, such a copolymer of branched PEG and a cationic polymer can be administered as the polyvalent cations of the present invention.

In another specific aspect, the cationic polymer block can have an average polymerization degree of 15 to 30, the cationic polymer block can be linked to the branched PEG, the branched PEG can be branched at one site, and the PEG chains extending from the branching site can each independently have an average molecular weight, for example, of 20 kD to 60 kD, 25 kD to 50 kD, or 30 kD to 40 kD. According to the present invention, such a copolymer of branched PEG and a cationic polymer can be administered as the polyvalent cations of the present invention.

In the present invention, examples of the cationic polymer or the cationic polymer portion include cationic natural amino acids and cationic non-natural amino acids, e.g., cationic natural amino acids such as histidine, tryptophan, ornithine, arginine, and lysine, and/or polymer blocks having a group, as a side chain, represented by —(NH—$(CH_2)_2)_p$—$NH_2$ (where p represents an integer of 1 to 5), e.g., polymer blocks of cationic non-natural amino acids having the aforementioned cationic side chain, e.g., polymer blocks of cationic non-natural amino acids such as aspartic acid or glutamic acid having the aforementioned cationic side chain. In an aspect of the present invention, the polycation block is a polymer block having a group, as a side chain, represented by —(NH—$(CH_2)_2)_p$—$NH_2$ (where p represents an integer of 1 to 5). Here, preferred examples of the cationic natural amino acids include histidine, tryptophan, ornithine, arginine, and lysine, more preferably arginine, ornithine, and lysine, further preferably ornithine and lysine, furthermore preferably lysine. In an aspect of the present invention, the cationic polymer or the cationic polymer portion can be polylysine or polyornithine.

In the polycation block, a cationic amino acid and an amino acid having a cationic side chain may be mixed. In an aspect of the present invention, the polycation block is a cationic natural amino acid, a cationic non-natural amino acid, or a polymer of monomer units containing a cationic natural amino acid and a cationic non-natural amino acid. In an aspect of the present invention, the monomer units in the polycation block are bound via peptide bonds. In a preferred aspect of the present invention, the cationic non-natural amino acid is an amino acid having a group, as a side chain, represented by —(NH—$(CH_2)_2)_p$—$NH_2$ (where p represents an integer of 1 to 5). In another aspect of the present invention, the polycation block can be a polycation block formed by polymerizing a cationic natural amino acid, and glutamic acid and aspartic acid modified with a group represented by —(NH—$(CH_2)_2)_p$—$NH_2$ (where p represents an integer of 1 to 5) in any order. In an aspect of the present invention, 40%, 50%, 60%, 70%, 80%, 90%, 95%, 98%, or 100% of the monomer units in the polymer has a group, as a side chain, represented by —(NH—$(CH_2)_2)_p$—$NH_2$ (where p represents an integer of 1 to 5).

Examples of the cationic polymer as an aspect of the present invention include polylysine or polyornithine having a branched PEG, wherein the PEG portion is a branched PEG having two PEGs with an average molecular weight of 20 to 50 kD, and the polylysine or polyornithine has an average polymerization degree of 20 to 70 or 30 to 60. In a preferred aspect, the PEG or branched PEG can be linked to the end of the cationic polymer. According to another aspect, examples thereof can include a polymer containing cationic monomers such as lysine and ornithine as the main backbone with 5% to 80% or 20% to 50% of the side chains of the monomer units modified with a hydrophilic polymer such as PEG or branched PEG (that is, a graft copolymer).

The polyvalent cations of the present invention can reduce the clearance function of the endothelial cells by covering the inner vascular surface of the liver sinusoidal endothelial cells and the inner vascular surface of the kidney vascular endothelial cells. Accordingly, the polyvalent cations of the present invention can be administered before, simultaneously with, or after administration of various drugs. In any case, in the case where the polyvalent cations and the drug are administered separately, the pharmacokinetics can be controlled when both are present in blood at the same time (in the case where the polyvalent cations are administered before administration of the drug, the drug is administered while the cationic polymer remains in blood, on the inner vascular surface of the liver sinusoidal endothelial cells, or on the inner vascular surface of the endothelial cells of the kidneys, whereas in the case where the polyvalent cations are administered after administration of the drug, the polyvalent cations are administered while the drug remains in blood). In an aspect, the polyvalent cations can be administered, for example, immediately before administration of the drug, such as 30 seconds or more, 1 minute or more, 2 minutes or more, 3 minutes or more, 4 minutes or more, or 5 minutes or more before administration of the drug. In an aspect, the polyvalent cations can be administered, for example, within 60 minutes, 50 minutes, 40 minutes, 30 minutes, 20 minutes, or 10 minutes before administration of the drug. In an aspect, the drug can be administered 10 minutes, 5 minutes, 4 minutes, 3 minutes, 2 minutes, 1 minute, 30 seconds, or immediately before administration of the polyvalent cations. The time from administration of the drug to administration of the polyvalent cations is preferably shorter. In the case of simultaneous administration, the drug and the polyvalent cations can be incorporated in an infusion bag to be administered, for example.

The cationic polymer of the present invention can reduce the clearance function of the endothelial cells by covering the inner vascular surface of the liver sinusoidal endothelial cells and the inner vascular surface of the kidney vascular endothelial cells. Accordingly, the cationic polymer of the present invention can be administered before, simultaneously with, or after administration of various drugs. In any case, in the case where the cationic polymer and the drug are administered separately, the pharmacokinetics can be controlled when both are present in blood at the same time (in the case where the cationic polymer is administered before administration of the drug, the drug is administered while the cationic polymer remains in blood, the cationic polymer remains on the inner vascular surface of the liver sinusoidal endothelial cells, or the cationic polymer remains on the inner vascular surface of the endothelial cells of the kidneys, whereas in the case where the cationic polymer is administered after administration of the drug, the cationic polymer is administered while the drug remains in blood). In an aspect, the cationic polymer can be administered, for example, immediately before administration of the drug, such as 30 seconds or more, 1 minute or more, 2 minutes or more, 3 minutes or more, 4 minutes or more, or 5 minutes or more before administration of the drug. In an aspect, the cationic polymer can be administered, for example, within 60 minutes, 50 minutes, 40 minutes, 30 minutes, 20 minutes, or 10 minutes before administration of the drug. In an aspect, the drug can be administered 10 minutes, 5 minutes, 4 minutes, 3 minutes, 2 minutes, 1 minute, 30 seconds, or immediately before administration of the cationic polymer. The time from administration of the drug to administration of the cationic polymer is preferably shorter. In the case of simultaneous administration, the drug and the cationic polymer can be incorporated in an infusion back to be administered, for example.

In an aspect of the present invention, the dosage and frequency of administration of the polyvalent cations of the present invention can be determined so as to reduce the clearance of the drug administered for a required time along with the timing of the administration of the drug (or before or after that). In an aspect of the present invention, the polyvalent cations of the present invention can be administered in a single dose or multiple doses so as to reduce the clearance of the drug administered for a required time along with the timing of the administration of the drug (or before or after that). In an aspect of the present invention, the administration may be bolus administration or infusion administration, depending on the purpose.

According to the present invention, the polyvalent cations reduce accumulation of carriers for drug delivery encapsulating nucleic acids (such as micelles and liposomes) in the liver sinusoidal endothelial cells or the endothelial cells of the kidneys. Accordingly, the polyvalent cations of the present invention can be used particularly for controlling the pharmacokinetics of carriers for drug delivery encapsulating nucleic acids.

According to the present invention, the cationic polymer reduces accumulation of carriers for drug delivery encapsulating nucleic acids (such as micelles and liposomes) in the liver sinusoidal endothelial cells or the endothelial cells of the kidneys. Accordingly, the cationic polymer of the present invention can be used particularly for controlling the pharmacokinetics of carriers for drug delivery encapsulating nucleic acids.

Examples of the nucleic acids include deoxyribonucleic acid (DNA) and ribonucleic acid (RNA), and modified nucleic acids such as Locked nucleic acid (LNA) and bridged nucleic acid (BNA), or hybrids of thereof. DNA is not specifically limited, but examples thereof include linear double-stranded DNA, linear single-stranded DNA, cyclic double-stranded DNA, and cyclic single-stranded DNA. RNA is not specifically limited, but examples thereof include siRNA, shRNA, micro RNA, messenger RNA (mRNA), transfer RNA (tRNA), ribosome RNA (rRNA), non-coding RNA (ncRNA), and double-stranded RNA, and derivatives of these RNAs.

When administered together with a carrier for drug delivery encapsulating nucleic acids (such as micelles and liposomes), the polyvalent cations can exist in a free form. That is, it is known that the polyvalent cations can directly form a complex with nucleic acids, but the polyvalent cations preferably exist in a free form (that is, without forming a complex with nucleic acids) in the present invention, since the polyvalent cations is used for covering the vascular endothelial cells of the liver or the kidney. The carrier for drug delivery encapsulating nucleic acids may be a lipid complex such as lipoplex, instead of an ion complex.

When administered together with a carrier for drug delivery encapsulating nucleic acids (such as micelles and liposomes), the cationic polymer can exist in a free form. That is, it is known that the cationic polymer can directly form a complex with nucleic acids, but the cationic polymer can exist in a free form (that is, without forming a complex with nucleic acids) in the present invention, since the cationic polymer covers the vascular endothelial cells of the liver or the kidney. As the cationic polymer, a cationic polymer different from the cationic polymer used in producing a carrier for drug delivery encapsulating nucleic acids can be used. The carrier for drug delivery encapsulating nucleic acids may be a lipid complex such as lipoplex, instead of an ion complex.

In an aspect of the present invention, a virus may be used as a carrier for enhancing the nucleic acid transfer efficiency into cells. For enhancing the nucleic acid transfer efficiency into cells, viral vectors such as retroviral vector, lentiviral vector, adenoviral vector, adeno-associated viral vector (such as AAV1, AAV2, AAV3, AAV4, AAV5, AAV6, AAV7, AAV8, AAV9, and AAV10), Sendai viral vector, measles viral vector, vaccinia viral vector, and herpes viral vector can be used as carriers. These vectors, for example, may have an expression unit (for example, nucleic acids operably linked to a promoter or an enhancer) that expresses the nucleic acids to be delivered in cells.

An embodiment of the present invention provides a method for administering a drug to a subject, comprising: administering polyvalent cations to the subject; and administering the drug to the subject. In an aspect of the present invention, the polyvalent cations and RNA are administered separately. In an aspect of the present invention, the polyvalent cations can be administered to the subject simultaneously with, before, or after administration of the drug. The polyvalent cations are biocompatible but can be administered in doses so as not to exert the dose limiting toxicity (DLT).

An embodiment of the present invention provides a method for administering a drug to a subject, comprising: administering a cationic polymer to the subject; and administering the drug to the subject. In an aspect of the present invention, the cationic polymer and RNA are administered separately. In an aspect of the present invention, the cationic polymer can be administered to the subject simultaneously with, before, or after administration of the drug. The cationic polymer is biocompatible but can be administered in doses so as not to exert the dose limiting toxicity (DLT).

An embodiment of the present invention provides a method for administering a carrier for drug delivery encapsulating nucleic acids to a subject, comprising: administering polyvalent cations to the subject; and administering the carrier for drug delivery encapsulating nucleic acids to the subject. An embodiment of the present invention provides a method for delivering nucleic acids to a tissue of a subject, comprising: administering polyvalent cations to the subject; and administering a carrier for drug delivery encapsulating nucleic acids to the subject. In an aspect of the present invention, the polyvalent cations can be administered to the subject simultaneously with administration of the carrier for drug delivery encapsulating nucleic acids, or before or after administration of the drug.

An embodiment of the present invention provides a method for administering a carrier for drug delivery encapsulating nucleic acids to a subject, comprising: administering a cationic polymer to the subject; and administering the carrier for drug delivery encapsulating nucleic acids to the subject. An embodiment of the present invention provides a method for delivering nucleic acids to a tissue of a subject, comprising: administering a cationic polymer to the subject; and administering a carrier for drug delivery encapsulating the nucleic acids to the subject. In an aspect of the present invention, the cationic polymer can be administered to the subject simultaneously with administration of the carrier for drug delivery encapsulating nucleic acids, or before or after administration of the drug.

Further, the inventors have found that micelles formed by a ternary copolymer containing a hydrophilic block, a temperature-responsive block, and a cationic block dramatically improve the stability of nucleic acids in blood and can deliver a large amount of nucleic acids, for example, to the brain tissue. Accordingly, the present invention provides a composition for use in delivering nucleic acids to an organ or a tissue (particularly, the brain), comprising micelles which comprise, for example, nucleic acids and a ternary copolymer containing a hydrophilic block, a temperature-responsive block and a cationic block, and which have the surfaces modified with glucose.

Such micelles can be prepared by the following procedure. That is, a ternary copolymer containing a hydrophilic block, a temperature-responsive block, and a cationic block is mixed with RNA in an aqueous solution with a temperature lower than the LCST so as to form micelles. After micelles are obtained, the temperature of the aqueous solution is increased to the LOST or higher, to change the temperature-responsive block from hydrophilic to hydrophobic. The micelles thus obtained are considered to encapsulate nucleic acids therein and have hydrophobic protective layers as their outer shells, and can maintain the encapsulated nucleic acids stably in blood. That is, the nucleic acids in these micelles are covered by the outer shells formed by the temperature-responsive block changed to hydrophobic.

In the case of a human, the LCST of the ternary copolymer is preferably 35° C. or less, considering that the blood temperature is about 36° C. to 37° C. Such temperature allows the state of micelles in blood to be maintained after administration. Further, considering that mRNA is prepared at about 0° C. to 4° C., the LCST is preferably 5° C. or more. An appropriate LCST is set preferably in consideration of various other situations. For example, the LCST can be set to 5° C. to 35° C., 10° C. to 32° C., or 25° C. to 32° C. Generally, water-soluble polymers have an LCST. In the present invention, any polymer having an LCST within such a temperature range can be appropriately used as the temperature-responsive block.

In an aspect of the present invention, the hydrophilic block of the ternary copolymer can be polyethylene glycol or poly(2-ethyl-2-oxazoline). The average molecular weight of the hydrophilic block can be, for example, 10 kD or more, 15 kD or more, 20 kD or more, 30 kD or more, or 40 kD or more. Further, the average molecular weight of the hydrophilic block can be, for example, 20 kD or less, 30 kD or less, 40 kD or less, or 50 kD or less.

In an aspect of the present invention, the temperature-responsive block of the ternary copolymer can be poly(N-isopropyl acrylamide), poly(2-n-propyl-2-oxazoline), or poly(2-isopropyl-2-oxazoline). The average molecular weight of the temperature-responsive block can be, for example, 3 kD or more, 5 kD or more, 7 kD or more, or 10 kD or more. Further, the average molecular weight of the temperature-responsive block can be, for example, 10 kD or less, 15 kD or less, or 20 kD or less.

In an aspect of the present invention, the polycationic block of the ternary copolymer can be a peptide containing natural or non-natural cationic amino acids as monomer units. The polycationic block of the ternary copolymer can be, for example, a peptide containing natural cationic amino acids such as lysine and ornithine as monomer units, e.g., polylysine or polyornithine. In an aspect of the present invention, the polycationic block of the ternary copolymer can be, for example, a peptide containing glutamic acid and aspartic acid having a carboxyl group modified with diethylenetriamine or triethylenetetraamine as monomer units, e.g., a homopolymer. The average polymerization degree of the polycationic block can be, for example, 30 or more, 40 or more, 50 or more, 60 or more, or 70 or more. Further, the average polymerization degree of the polycationic block can be 70 or less, 80 or less, 90 or less, or 100 or less.

In an aspect of the present invention, the hydrophilic block is polyethylene glycol or poly(2-ethyl-2-oxazoline), the temperature-responsive block is poly(2-n-propyl-2-oxazoline), and the polycationic block is polylysine or polyornithine, in the ternary copolymer. In an aspect of the present invention, the hydrophilic block is polyethylene glycol, the temperature-responsive block is poly(2-n-propyl-2-oxazoline), and the polycationic block is polylysine, in the ternary copolymer.

In the present invention, micelles formed by the aforementioned ternary copolymer and encapsulating the nucleic acids stabilized by hydrophobic protective layers can be used as the carrier for drug delivery encapsulating nucleic acids. In the present invention, vesicles, e.g., lipid-based vesicles, e.g., liposomes, e.g., lipid-based vesicles (for example, lipoplex) such as Invivofectamine (trademark) also can be used as the carrier for drug delivery encapsulating nucleic acids. These vesicles preferably have surfaces covered with a hydrophilic polymer.

In the present invention, a carrier with its outer surface covered with GLUT1 ligand such as glucose can be used as the carrier for drug delivery to be used in delivering nucleic acids to the brain (refer to WO 2015/075942A1 for details of the principle). When this carrier is administered according to the following dosing regimen, the accumulation in the brain is improved. That is, the dosing regimen comprises: administering the composition to the subject who has been fasted or induced to have hypoglycemia; and inducing an increase in blood sugar level in the subject.

In the present invention, the nucleic acids to be delivered to the spleen are not specifically limited, but examples thereof include nucleic acids encoding factors that enhance the functions of the spleen (for example, immune function). Examples of the nucleic acids encoding factors that enhance the immune function include nucleic acids encoding peptides or proteins that serve as antigens of immune cells. Such nucleic acids can increase the immune function against specific antigens and give a preventive effect or a therapeutic effect against infection, cancer, and the like. Examples of the nucleic acids encoding peptides or proteins that serve as antigens of immune cells include nucleic acids encoding peptide vaccines, particularly, peptides used as tumor-specific peptide vaccines (for example, HLA-restricted peptides such as HLA-A24- or HLA-A2-restricted peptides including HLA-A2:01- or HLA-A24:01-restricted peptides). Such peptides have been already developed a lot, and many of them have been clinically studied. Those skilled in the art would be able to appropriately select and use them in the present invention. Dendritic cells are present in the spleen, and peptides are expressed on these dendritic cells. Thereby, such peptides are presented to immune cells. The immune cells become responsive to the peptides in the spleen, the immune function against the peptides increases, and cancer cells expressing the peptides on the surface of the cells can be attacked. Thereby, it is expected that the anti-tumor effect is eventually enhanced. The present invention provides use of AAV8 for delivering nucleic acids to the spleen. The present invention provides use of AAV8 in the manufacture of medicament for use in delivering nucleic acids to the spleen. The present invention provides use of a combination of AAV8 and polyvalent cations for delivering nucleic acids to the spleen. The present invention provides use of a combination of AAV8 and polyvalent cations in the manufacture of medicament for use in delivering nucleic acids to the spleen. The present invention provides use of polyvalent cations for use in delivering AAV8 to the spleen. The present invention provides use of polyvalent cations in the manufacture of medicament for use in delivering AAV8 to the spleen. The present invention provides a pharmaceutical containing polyvalent cations for use in delivering AAV8 to the spleen.

In the present invention, examples of heart diseases or disorders to be treated include myocardial infarction, but there is no limitation to such examples. The present invention provides a method for treating such heart diseases or disorders in a subject in need thereof, comprising administering AAV to be used in combination with the polyvalent cations of the present invention. Here, AAV9 can be used as the AAV, for example. AAV9, for example, can have genes encoding a factor having a cardiac regenerative effect such as vascular endothelial growth factor (VEGF). The present invention provides use of AAV9 for delivering nucleic acids to the heart. The present invention provides use of a combination of AAV9 and polyvalent cations in the manufacture of medicament for use in delivering nucleic acids to the heart. The present invention provides use of AAV9 for delivering nucleic acids to the heart. The present invention provides use of a combination of AAV9 and polyvalent cations in the manufacture of medicament for use in delivering nucleic acids to the heart. The present invention provides use of polyvalent cations for use in delivering AAV9 to the heart. The present invention provides use of polyvalent cations in the manufacture of medicament for use in delivering AAV9 to the heart. The present invention provides a medicament for use in delivering AAV9 to the heart, the medicament comprising polyvalent cations.

In this description, the term "GLUT1 ligand" means a substance that specifically binds to GLUT1. Various ligands are known as the GLUT1 ligand, and there is no specific limitation, but examples thereof include molecules such as glucose and hexose. Any GLUT1 ligand can be used for preparing carriers or conjugates in the present invention, instead of glucose. The GLUT1 ligand preferably has an affinity for GLUT1 equal to or greater than that of glucose. Also, 2-N-4-(1-azi-2,2,2-trifluoroethyl) benzoyl-1,3-bis(D-mannose-4-yloxy)-2-propylamine (ATB-BMPA), 6-(N-(7-nitrobenz-2-oxa-1,3-diazol-4-yl) amino)-2-deoxyglucose (6-NBDG), 4,6-O-ethylidene-α-D-glucose, 2-deoxy-D-glucose, and 3-O-methyl glucose are known to bind to GLUT1, and these molecules can be used in the present invention as GLUT1 ligands.

In this description, the phrase "inducing hypoglycemia" means lowering blood sugar level in a subject more than would otherwise have been exhibited if not treated. Examples of the method for inducing hypoglycemia include administration of diabetes drugs. When inducing hypoglycemia, it is acceptable, for example, to take other drugs or beverages such as water, as long as the purpose of inducing hypoglycemia is achieved. The induction of hypoglycemia may be accompanied by other treatments that do not substantially affect the blood sugar.

In this description, the phrase "being fasted" means that the subject is fasted, for example, for 3 hours or more, 4 hours or more, 5 hours or more, 6 hours or more, 7 hours or more, 8 hours or more, 9 hours or more, 10 hours or more, 11 hours or more, 12 hours or more, 13 hours or more, 14 hours or more, 15 hours or more, 16 hours or more, 17 hours or more, 18 hours or more, 19 hours or more, 20 hours or more, 21 hours or more, 22 hours or more, 23 hours or more, 24 hours or more, 25 hours or more, 26 hours or more, 27 hours or more, 28 hours or more, 29 hours or more, 30 hours or more, 31 hours or more, 32 hours or more, 33 hours or more, 34 hours or more, 35 hours or more, 36 hours or more, 37 hours or more, 38 hours or more, 39 hours or more, 40 hours or more, 41 hours or more, 42 hours or more, 43 hours or more, 44 hours or more, 45 hours or more, 46 hours or more, 47 hours or more, or 48 hours or more. Fasting causes the subject to have hypoglycemia. The fasting period is determined by a doctor or the like in consideration of the health condition of the subject and is preferably, for example, a period of time equal to or longer than the time when the subject reaches the fasting blood sugar. The fasting period may be, for example, equal to or longer than a period of time in which the expression of GLUT1 on the inner vascular surface of the cerebral vascular endothelial cells increases or reaches the plateau. The fasting period can be one of the aforementioned periods, for example, 12 hours or more, 24 hours or more, or 36 hours or more. Further, fasting may be accompanied by other treatments that do not substantially affect the blood sugar level or the expression of GLUT1 on the inner vascular surface.

In this description, the phrase "inducing an increase in blood sugar level" means to increase the blood sugar level in a subject with hypoglycemia induced or a subject maintained in the state of hypoglycemia. The blood sugar level can be increased by various methods known to those skilled in the art, such as administration of substances that induce an increase in blood sugar level, e.g., administration of monosaccharides that induce an increase in blood sugar level such as glucose, fructose, and galactose, administration of polysaccharides that induce an increase in blood sugar level such as maltose, or ingestion of carbohydrates that induce an increase in blood sugar level such as starch, or having a meal.

In this description, the phrase "controlling the blood sugar" means to induce hypoglycemia and thereafter increase the blood sugar level in a subject. After inducing hypoglycemia in the subject, the blood sugar level of the subject can be maintained at a low level. The time to maintain the blood sugar level of the subject at a low level can be, for example, 0 hours or more, 1 hour or more, 2 hours or more, 3 hours or more, 4 hours or more, 5 hours or more, 6 hours or more, 7 hours or more, 8 hours or more, 9 hours or more, 10 hours or more, 11 hours or more, 12 hours or more, 13 hours or more, 14 hours or more, 15 hours or more, 16 hours or more, 17 hours or more, 18 hours or more, 19 hours or more, 20 hours or more, 21 hours or more, 22 hours or more, 23 hours or more, 24 hours or more, 25 hours or more, 26 hours or more, 27 hours or more, 28 hours or more, 29 hours or more, 30 hours or more, 31 hours or more, 32 hours or more, 33 hours or more, 34 hours or more, 35 hours or more, 36 hours or more, 37 hours or more, 38 hours or more, 39 hours or more, 40 hours or more, 41 hours or more, 42 hours or more, 43 hours or more, 44 hours or more, 45 hours or more, 46 hours or more, 47 hours or more, or 48 hours or more. Thereafter, the blood sugar level can be increased. In this description, within the meaning of the phrase "maintaining the blood sugar", it is accepted to, for example, take other drugs or beverages such as water as long as the purpose of maintaining hypoglycemia in the subject is achieved. The induction of hypoglycemia may be accompanied by other treatments that do not substantially affect the blood sugar.

In the dosing regimen according to the present invention, the composition can be administered to the subject, simultaneously, continuously, or sequentially with the induction of the increase of blood sugar level in the subject. The dosing regimen may or may not have an interval between the administration of the composition to the subject and the induction of the increase of blood sugar level in the subject. In the case where the composition is administered simultaneously with the induction of the increase of blood sugar level in the subject, the composition may be administered to the subject in a form mixed with a drug that induces an increase in blood sugar level or may be administered in a form different from the drug that induces an increase in blood sugar level in the subject. Further, in the case where the composition is administered to the subject continuously or sequentially with the induction of the increase of blood sugar level in the subject, the composition may be administered to the subject either before or after the induction of the increase of blood sugar level in the subject, but the composition can be preferably administered before the induction of the increase of blood sugar level in the subject. In the case where an increase in blood sugar level is induced in the subject before the administration of the composition to the subject, the composition is preferably administered to the subject within 1 hour, 45 minutes, 30 minutes, 15 minutes, or 10 minutes, after the induction of the increase of blood sugar level in the subject. Meanwhile, in the case where an increase in blood sugar level is induced in the subject after the administration of the composition to the subject, an increase in blood sugar level is preferably induced in the subject within 6 hours, 4 hours, 2 hours, 1 hour, 45 minutes, 30 minutes, 15 minutes, or 10 minutes, after the administration of the composition to the subject. The cycle of the aforementioned dosing regimen may be performed twice or more. The timing of the glucose administration and the sample administration can be determined depending on the timing of passing through the blood-brain barrier.

The micelles of the present invention which are formed by the aforementioned ternary copolymer or the like and in which the nucleic acids encapsulated by hydrophobic protective layers are stabilized can be used for delivery to the cerebral vascular endothelial cells. Further, the roles of glucose in the present invention are the same as in the blood-nerve barrier, the blood-retina barrier, and the blood-cerebrospinal fluid barrier. In particular, GLUT1 is expressed in the vascular endothelial cells during hypoglycemia also in the blood-nerve barrier, the blood-retina barrier, and the blood-cerebrospinal fluid barrier. Accordingly, the micelles of the present invention which are formed by the aforementioned ternary copolymer or the like and in which the nucleic acids encapsulated by hydrophobic protective layers are stabilized can be used for passage through the blood-nerve barrier, the blood-retina barrier, and the blood-cerebrospinal fluid barrier. Further, the micelles of the present invention which are formed by the ternary copolymer or the like and in which contain the nucleic acids encapsulated by hydrophobic protective layers are stabilized can be used for delivery to the vascular endothelial cells existing in the blood-nerve barrier, the blood-retina barrier, and the blood-cerebrospinal fluid barrier.

EXAMPLES

Example 1: Effect of Administration of Polyvalent Cations on Accumulation of Micelles for Drug Delivery in the Liver

[Materials]

As micelles for drug delivery, triblock polymer micelles of PEG (molecular weight: 11 k)-b-PnProx (molecular weight: 8 k)-b-PLys (polymerization degree: 43) with a surface modified with glucose were used. The glucose modification of the surface was for facilitating the delivery of the micelles to the brain. According to the disclosure of WO 2015075942A1, the micelles modified with glucose were administered to a subject in the fasted state, and the blood sugar level of the subject was increased before and after the administration. As a result, the micelles were remarkably incorporated into the brain with the increase of the blood sugar level.

A polymer (DIG-PEG) having a glucose derivative DIG at the PEG end was synthesized according to WO 2015075942A1. Further, a copolymer of DIG-PEG with PnProx and PLys was obtained by linking PnProx-b-PLys synthesized according to the description in European Polymer Journal, 2017, 88, 553-561 to Glc-PEG. The synthetic scheme of the triblock copolymer was as shown in schemes 1 to 4 below.

Scheme 1

[Formula 1]

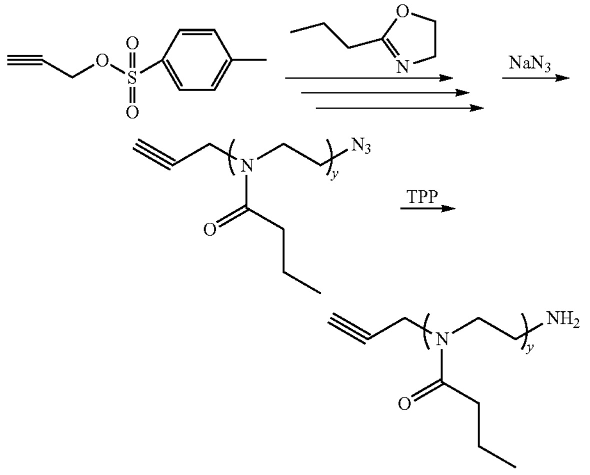

Scheme 2

[Formula 2]

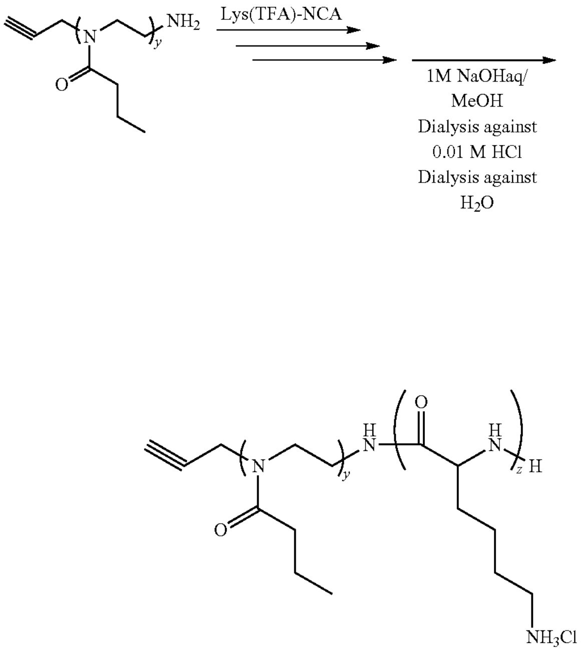

Scheme 3

[Formula 3]

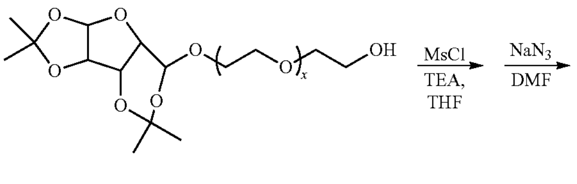

-continued

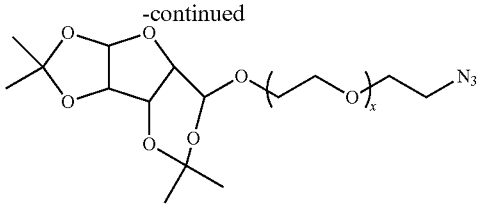

DIG-PEG-azide

Scheme 4

[Formula 4]

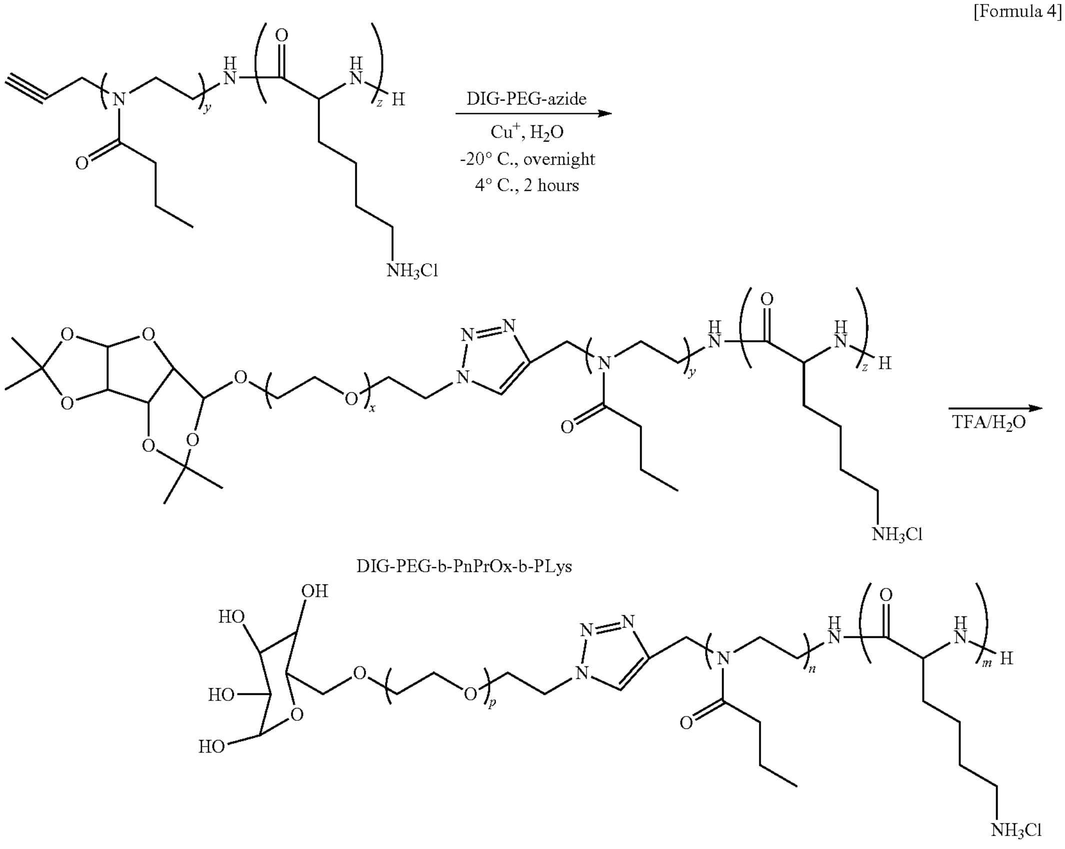

DIG-PEG-b-PnPrOx-b-PLys

Glc-PEG-b-PnPrOx-b-PLys

Specifically, a block copolymer alkyne-PnProx-b-PLys consisting of a temperature-responsive chain Poly(2-n-propyl-2-oxazoline) (PnProx) and a cationic chain Poly(L-Lysine) (PLys) and having an alkyne end was synthesized, as follows.

First, a polymerization initiator propargyl p-toluenesulfonate (61 mg, 0.29 mmol) was dissolved in 7 mL of acetonitrile, and 2-n-propyl-2-oxazoline (2.5 g, 22 mmol) was added thereto. After the reaction solution was allowed to react at 42° C. for 6 days, sodium azide (380 mg, 5.8 mmol) was added thereto, followed by stirring at 70° C. for 1 hour, to stop the polymerization reaction. All the processes were performed in an Ar atmosphere. The propargyl p-toluenesulfonate used herein was purchased from Tokyo Chemical Industry Co., Ltd. and purified by distillation using diphosphorus pentoxide purchased from FUJIFILM Wako Pure Chemical Corporation as a dehydrating agent. 2-n-Propyl-2-oxazoline was purchased from Tokyo Chemical Industry Co., Ltd. and purified by distillation using calcium hydride purchased from Sigma-Aldrich as a dehydrating agent. Acetonitrile as a reaction solvent was purchased from FUJIFILM Wako Pure Chemical Corporation and purified by distillation using calcium hydride as a dehydrating agent. Sodium azide was purchased from FUJIFILM Wako Pure Chemical Corporation and used as it was. After the polymerization reaction, the reaction solution was dialyzed against water 5 times, followed by freeze drying, to obtain alkyne-PnProx-$N_3$ having an azide end. It turned out from the analyses by MALDI-TOF MS (UltraFlextreme, Bruker) and 1H-NMR (ESC400, JEOL) that the PnProx obtained had a molecular weight of 8.3 k.

Subsequently, the azide end of alkyne-PnProx-$N_3$ was converted into an amine end by the Staudinger reaction. Alkyne-PnProx-$N_3$ (830 mg, 0.10 mmol) was dissolved in 20 mL of methanol, and triphenylphosphine (530 mg, 2.0 mmol) was added thereto, followed by stirring at 40° C. for 3 hours. Subsequently, 20 mL of pure water was added thereto, followed by cooling with ice, and unreacted triphenylphosphine or the like was removed by filtration. The solution obtained was dialyzed against pure water 3 times and was then collected by freeze drying. The alkyne-PnProx-$NH_2$ obtained was further purified using an open column with CM-Sephadex C50 purchased from GE Healthcare as a column filler. The methanol and triphenylphosphine used herein were respectively purchased from Sigma-Aldrich and Tokyo Chemical Industry Co., Ltd.

Lys(TFA)-NCA was polymerized from the alkyne-PnProx-$NH_2$ purified and collected above, followed by deprotection of a TFA group with a base, to obtain alkyne-PnProx-b-PLys. The alkyne-PnProx-$NH_2$ (330 mg, 0.040 mmol) was freeze-dried using dioxane. This was dissolved in 2 mL of DMF (DMF (1M TU)) in which thiourea had been dissolved at a concentration of 1 M to prepare an initiator solution. Separately, Lys (TFA)-NCA (480 mg, 1.8 mmol) was measured into a flask in an Ar bag and dissolved in 6 mL of DMF (1M TU). The Lys (TFA)-NCA solution prepared was added to the initiator solution in an Ar atmosphere, followed by stirring at 25° C. for 3 days, to perform a polymerization reaction. After the reaction solution was dialyzed against water 5 times, followed by freeze drying, to obtain PnProx-b-Poly(L-Lysine) (TFA) (PLys (TFA)). Subsequently, 500 mg of the alkyne-PnProx-b-PLys (TFA) obtained was measured and dissolved in 25 mL of methanol. To the mixture, was added 7.5 mL of a 1M NaOH solution, followed by reaction at 35° C. for 12 hours. After the reaction, dialysis against 0.01 M HCl was performed 3 times, and then dialysis against water was performed 3 times, to collect PnProx-b-PLys by freeze drying. It was confirmed by SEC (AKTA-explorer, GE Healthcare) using a column Superdex 200 of GE Healthcare that the material recovered had a single peak molecular weight distribution. Further, it turned out from analysis by 1H-NMR (ESC400, JEOL) that Lys was 43 in the polymer obtained. Here, the Lys (TFA)-NCA was synthesized by Fuchs-Farthing according to Non Patent Literature (J. Polym. Sci. Part A Polym. Chem. 2003, 41 1167-1187). The dioxane used was purchased from FUJIFILM Wako Pure Chemical Corporation. The DMF (1M TU) was adjusted by dissolving thiourea purchased from Sigma-Aldrich in a dehydrated solvent purchased from KANTO CHEMICAL CO., INC. The 1M NaOH solution was prepared by diluting a 5M NaOH solution purchased from NACALAI TESQUE, INC. with pure water. The 0.01 M HCl was prepared by diluting concentrated hydrochloric acid purchased from KOSO CHEMICAL CO. LTD. with pure water.

Further, as disclosed in the literature Bioconjugate, 2007, 18, 2191-2196, an OH end of DIG-PEG-OH was converted into an azide group. First, DIG-PEG-OH (550 mg, 0.050 mmol) was freeze-dried with benzene. This was dissolved in 20 mL of THE, and triethylamine (25 UL, 0.20 mmol) was added thereto to prepare a PEG solution. Methane sulfonyl chloride (16 μL, 0.20 mmol) was measured into another flask and diluted with 5 mL of THE. Under water cooling, the PEG solution adjusted above was added to the methane sulfonyl chloride diluent, followed by overnight reaction. The reaction was performed in an Ar atmosphere. The reactant was collected by reprecipitation with 500 mL of diethyl ether. It turned out from analysis by 1H-NMR (ESC400, JEOL) that the sample collected was DIG-PEG-Ms with a mesylated end. The DIG-PEG-Ms (440 mg, 0.044 mmol) obtained was dissolved in 20 mL of DMF, and sodium azide (286 mg, 4.4 mmol) was added thereto, followed by stirring at 50° C. for 3 days. The THF and DMF used were super dehydrated solvents purchased from KANTO CHEMICAL CO., INC. The triethylamine was purchased from FUJIFILM Wako Pure Chemical Corporation and purified by distillation using calcium hydride as a dehydrating agent. The mesyl chloride used was purchased from NACALAI TESQUE, INC. and distilled using diphosphorus pentoxide as a dehydrating agent. The sodium azide was purchased from FUJIFILM Wako Pure Chemical Corporation and used as it was.

Subsequently, Alkyne-PnProx-PLys and DIG-PEG-$N_3$ were coupled by Click Chemistry. Alkyne-PnProx-PLys (31 mg, 0.0020 mmol) was dissolved in 2 mL of water, and 20 μL each of a 1 M $CuSO_4$ solution and a 1 M sodium ascorbate solution were added thereto, followed by stirring. Separately, DIG-PEG-$N_3$ (110 mg, 0.01 mmol) was dissolved in 2 mL of water and was added to the Alkyne-PnProx-PLys solution. This was left standing at −20° C. overnight and then was melted at 4° C. over 2 hours. The reaction solution was dialyzed against water 5 times, followed by freeze drying, to collect a product. The product collected herein included Glc-PEG-$N_3$, which had been excessively added in order to completely react Alkyne-PnProx-PLys, and unreacted Alkyne-PnProx-PLys, other than the triblock copolymer. Focusing on the difference in molecular weight between such unreacted materials and the triblock copolymer as a product, purification work was performed by SEC. Finally, DIG was converted into glucose using TFA as disclosed in WO 2015075942A1, to prepare Glc-PEG-b-PnProx-b-PLys.

For checking the progress of coupling and the purification work by SEC, SEC (AKTAexplorer, GE Healthcare) using a column Superdex 200 of GE Healthcare was used.

The lower critical solution temperature (LCST) of the triblock copolymer was about 30° C.

Next, a cationic polymer having a biocompatibility enhanced by linking hydrophilic blocks was synthesized as the polyvalent cations. Specifically, branched poly(ethylene glycol)-b-poly(L-lysine) (polymerization degree: 20) (which may be hereinafter referred to as "bPEG-b-PLL", "PEGasus-PLL", or "PEGasus-PLL (37×2-20)"), which is a block catiomer having branched PEG (molecular weight: 37000×2), was synthesized.

To obtain branched poly(ethylene glycol)-b-poly(L-lysine), branched polyethylene glycol (bPEG) (molecular weight: 37000×2) and having a primary amine structure at an end, purchased from NOF CORPORATION, was used as an initiator, and Lysine (TFA)-NCA synthesized by Fuchs-Farthing according to Non Patent Literature (J. Polym. Sci. Part A Polym. Chem. 2003, 41 1167-1187) was polymerized, followed by treatment with a base.

Specifically, in the synthesis of bPEG-PLL, bPEG (740 mg, 0.010 mmol) having a primary amine was first freeze-dried with benzene purchased from NACALAI TESQUE, INC. Subsequently, thiourea (TU) purchased from Sigma-Aldrich was dissolved in dehydrated N,N-dimethylformamide (DMF) purchased from KANTO CHEMICAL CO., INC. to prepare DMF (1M TU) with a concentration of 1 M as a reaction solvent. The freeze-dried bPEG was dissolved in 10 mL of DMF (1M TU). Subsequently, 59 mg (0.22 mmol) of Lys (TFA)-NCA was measured into a flask in an Ar bag and dissolved in 2 mL of DMF. The Lys (TFA)-NCA solution prepared was added to the bPEG solution in an Ar atmosphere, followed by stirring at 25° C. for 3 days. The reaction solution was titrated against 300 mL of a 1:9 mixed solution of methanol (Sigma-Aldrich) and diethyl ether (SHOWA-ETHER), to reprecipitate a copolymer bPEG-PLL (TFA). The bPEG-PLL (TFA) obtained was collected by filtration, followed by vacuum drying. 500 mg of the bPEG-PLL (TFA) obtained was measured and dissolved in 25 mL of methanol. Subsequently, 7.5 mL of 1M NaOH was added to the bPEG-PLL (TFA) solution, followed by stirring at 35° C. for 12 hours, to deprotect the TFA group. After the reaction, dialysis against 0.01 M HCl was performed 3 times, and then dialysis against water was performed 3 times, to collect bPEG-PLL by freeze drying. The bPEG-PLL obtained was analyzed by SEC (LC2000 system, available from JASCO Corporation) using a column superdex 200 of GE Healthcare and 1H-NMR (ESC400, JEOL).

Polyplex micelles were formed from the triblock polymer obtained and mRNA. Specifically, the triblock polymer was mixed with mRNA at 4° C. with an electric charge ratio of 2, and the mixture was left standing at 37° C., so that a hydrophobic layer was formed in the triblock polymer to encapsulate mRNA, to obtain polyplex micelles having the hydrophobic layer as a protective layer of mRNA.

The mRNA was prepared by in-vitro transcription of a template DNA using a mMESSAGE mMACHINE T7 Ultra Kit (Ambion) and poly(A) modification using a poly(A) tail kit (Ambion). As the template DNA, a pCMV-Gluc control plasmid purchased from New England Biolabs, Inc. was used.

As the pDNA, pCAG-Luc2 provided by Riken BioResource Research Center and having a CAG promoter encoding luciferase was used.

(1) Change in Biokinetics of Polyplex Micelles by Polyvalent Cations

[Experiment]

In this experiment, biokinetics of mRNA were compared between the case where the glucose-modified polyplex micelles were administered alone to a fasted mouse (micelle-only administration group) and the case where a cationic polymer (PEGasus-PLL) were administered in addition to the same amount of the glucose-modified polyplex micelles (polyvalent cation administration group). The mRNA used in this experiment was fluorescently labeled in advance with a Label IT Tracker Cy5 Kit (Mirus Bio LLC).

Specifically, each mouse was fasted overnight to be starved. A 20% glucose solution was i.p. administered to the mouse. 30 minutes later, 300 μL of a solution obtained by adding 100 μL of HEPES buffer to 200 μL of a polyplex micelle solution adjusted to a mRNA concentration of 200 ng/μL was administered to the micelle-only administration group, and 100 μL of a PEGasus-PLL solution with a concentration adjusted to an electric charge ratio of 3 with respect to the mRNA to be administered was administered to the polyvalent cation administration group in addition to 200 μL of a polyplex micelle solution adjusted to a mRNA concentration of 200 ng/μL (total of 300 μL). 30 minutes after the administration, whole blood was collected and perfused with PBS. Thereafter, the mouse was dissected to extract organs (liver, kidney, and brain). The whole organs collected were ground with a Lysis buffer (Promega Corporation) and a Multi-Beads Shocker (Yasui Kikai Corporation), and the Cy5 fluorescence of the suspension was measured with a plate reader (Infinite M100 Pro, Tecan Trading AG), to evaluate the distribution of micelles in each organ. The total dose was taken as 100%, and the amount (%) accumulated in the organ was determined. The results were as shown in FIGS. 1 and 2.

Figure 2:
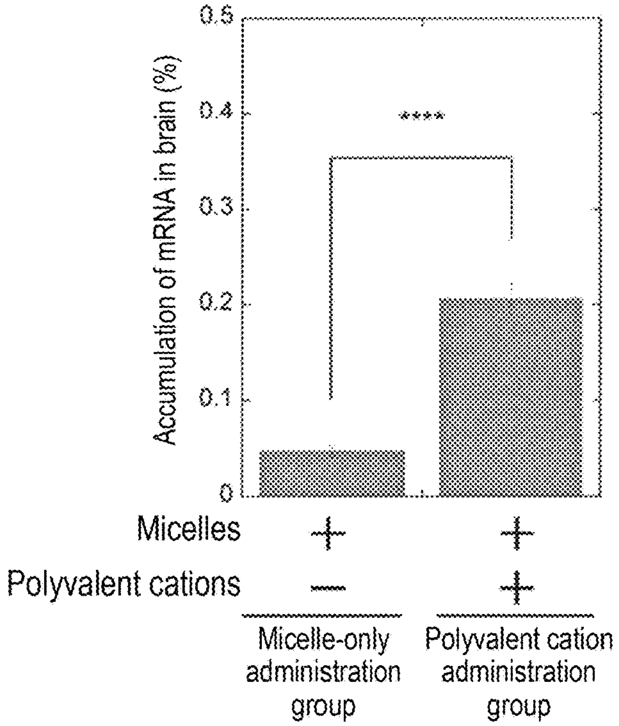
FIG. 2 is a graph showing the effect of a cationic polymer on accumulation of a drug in the brain.

As shown in FIG. 1, the amount of mRNA accumulated in the liver was less than 30% in the micelle-only administration group, whereas the amount accumulated was about a little more than 10% in the polyvalent cation administration group. It was shown that the amount accumulated in the liver was reduced to half or less. Further, as shown in FIG. 1, the amount of mRNA accumulated in the kidneys was about 7% in the micelle-only administration group, whereas it was about 5% in the polyvalent cation administration group. It was shown that the amount accumulated in the kidneys was reduced to about 70%.

Next, the amount of mRNA delivered to the brain was evaluated based on the amount of mRNA accumulated in the brain tissue. As a result, the amount of mRNA accumulated in the brain tissue was as large as 0.05%, even when micelles were administered alone, as shown in FIG. 2. This means that the polyplex micelles themselves extremely remarkably stabilized mRNA (mRNA is unstable in blood and would become below the detection limit in a few seconds). Further, in the polyvalent cation administration group, the amount of mRNA delivered to the brain was further improved as much as 5 times or more.

Figure 2A:
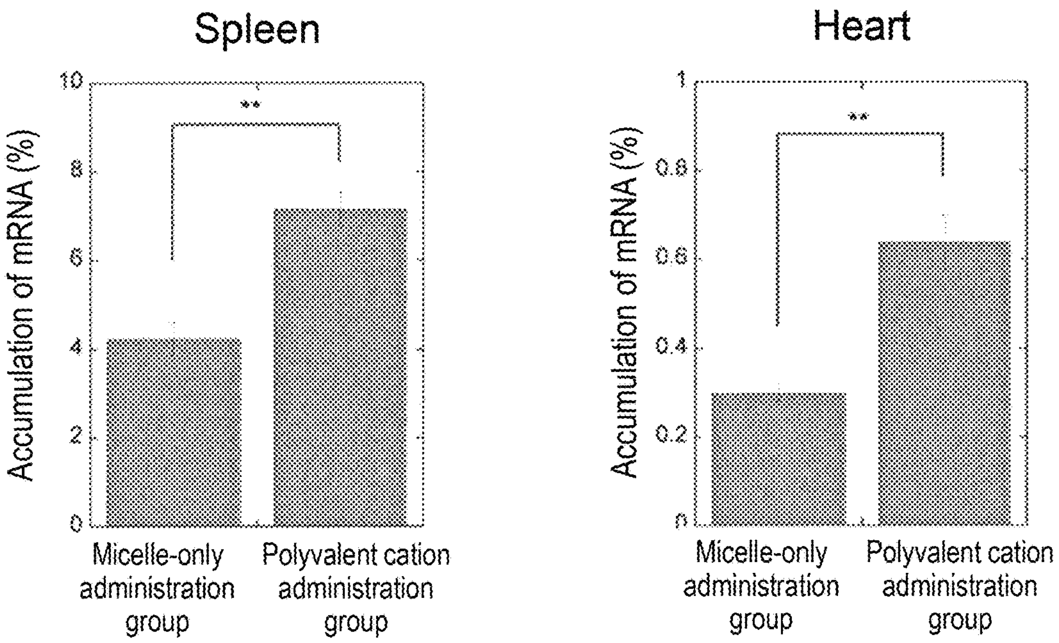
FIG. 2A includes graphs showing that accumulation of mRNA increases in organs other than the liver and kidney.

Further, the amounts of mRNA accumulated in other organs such as spleen and heart were evaluated. As a result, both the amount of mRNA accumulated in the spleen and the amount of mRNA accumulated in the heart significantly increased in the polyvalent cation administration group, as shown in FIG. 2A.

Further, the decrease in the amount of mRNA accumulated in the liver and kidneys was considered to be related to the ability of the liver and kidney to excrete mRNA from blood. Accordingly, it was revealed that the polyvalent cations had an effect of reducing the ability of the liver and kidney to excrete mRNA from blood and thereby increasing distribution of mRNA, that is, distribution of the drug in organs other than the liver and kidney. In the experiment of delivery to the brain in the aforementioned example, the blood sugar was controlled (by fasting and glucose administration), and micelles were coated with glucose, in order to promote the selective accumulation in the brain. Accordingly, in a system aiming at such selective mRNA delivery, the reduction of the ability to excrete mRNA and the increase of the retention in blood enhanced selective accumulation of mRNA in the brain. Meanwhile, in the aforementioned example, selective accumulation in the spleen and heart was not particularly controlled. However, since the amounts of mRNA accumulated in organs such as spleen and heart were improved, the cationic polymer was considered to have an effect of promoting accumulation of the drug in organs other than liver and kidneys through the effect of improving the retention of mRNA in blood.

(2) Change in Biokinetics of Lipid-Based mRNA Complex by Polyvalent Cations

Invivofectamine (trademark) is commercially available from Invitrogen as a reagent for delivering RNA to the liver. Invivofectamine (trademark) is a reagent for systemic administration of lipid-based mRNA and is particularly suitable for delivering mRNA to the liver.

Here, Invivofectamine (trademark) and mRNA were mixed according to the manufacturer protocol to form a lipid-based mRNA complex. The mRNA used in this experiment was fluorescently labeled in advance with a Label IT Tracker Cy5 Kit (Mirus Bio LLC).

100 μL of a PEGasus-PLL solution adjusted to a concentration of 12.5 mg/mL was intravenously administered to a mouse. 5 minutes later, 200 μL of the invivofectamine solution adjusted above was i.v. administered. 30 minutes after the administration, whole blood was collected and perfused with PBS. Thereafter, the mouse was dissected to extract organs (liver and kidney). As a negative control group to check the effect of addition of the polymer, comparison with a group in which 200 μL of the solution adjusted above was intravenously administered to a mouse without the prior administration of the polymer additive was performed. The organs collected were ground with a Lysis buffer (Promega Corporation) and a Multi-Beads Shocker (Yasui Kikai Corporation), and the fluorescence of Cy5 in the suspension was measured with a plate reader (Infinite M100 Pro, Tecan Trading AG), to evaluate the distribution of micelles in each organ.

Figure 3:
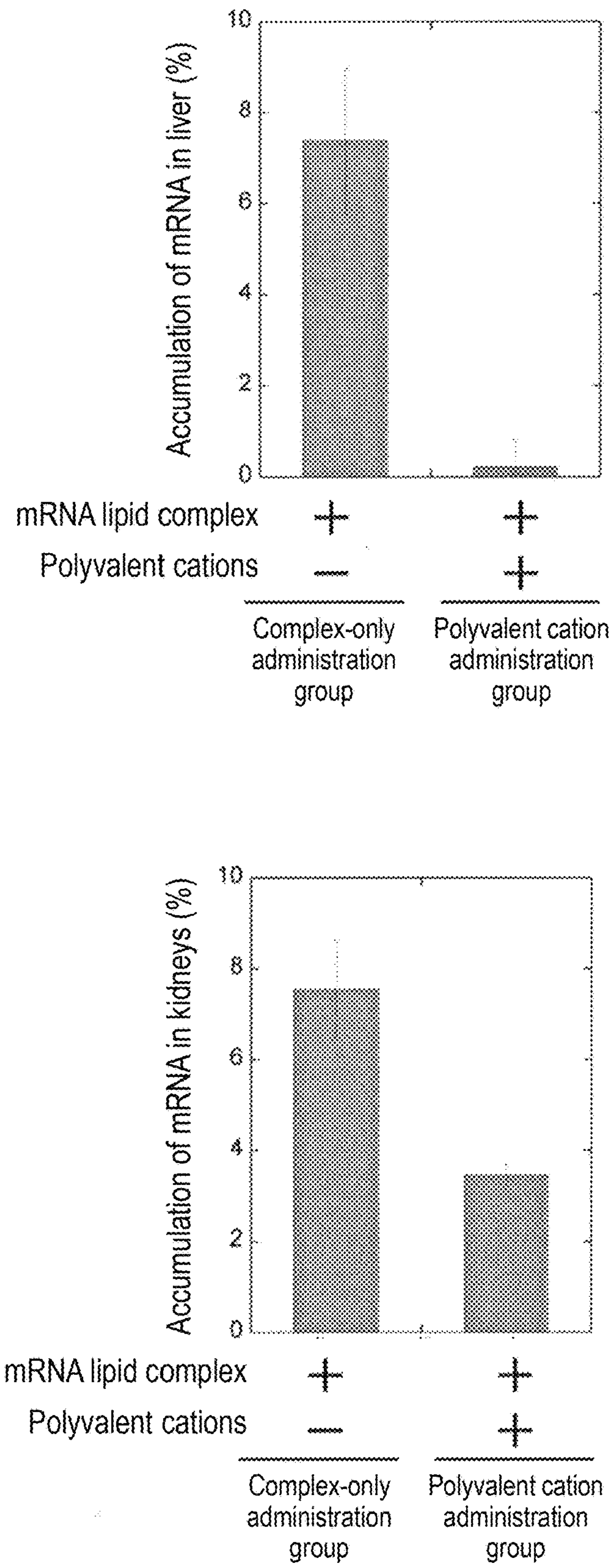
FIG. 3 includes graphs showing the effects of a cationic polymer on accumulation of a carrier (lipoplex) in the liver (upper panel) and the kidneys (lower panel).

The results were as shown in FIG. 3. As shown in the upper panel in FIG. 3, the amount of mRNA accumulated in the liver was 7% or more in the case where the complex was administered alone, whereas the amount accumulated was 0.5% or less in the case where the polyvalent cations were administered in advance. It was revealed from this that the prior administration of the polyvalent cations dramatically reduced the accumulation of the mRNA complex in the liver.

Further, as shown in the lower panel in FIG. 3, the amount of mRNA accumulated in the kidneys was 8% or less when administered alone, whereas the amount accumulated was 4% or less in the case where the polyvalent cations were administered in advance. It was revealed from this that the polyvalent cations also reduced the accumulation of the mRNA complex in the kidney.

Figure 3A:
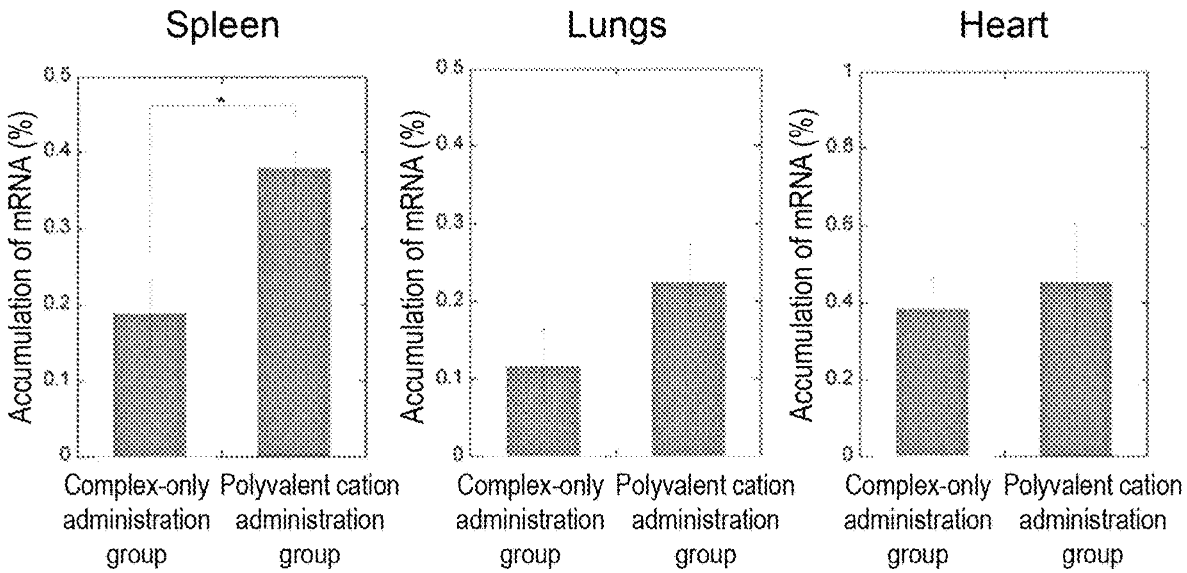
FIG. 3A includes graphs showing that accumulation of mRNA increases in organs other than the liver and kidney.

Further, the amounts of mRNA accumulated in other organs such as spleen and heart were evaluated also for lipoplex. As a result, the amount of mRNA accumulated in the spleen, the amount of mRNA accumulated in the lungs, and the amount of mRNA accumulated in the heart all significantly increased in the polyvalent cation administration group, as shown in FIG. 3A. It was suggested from this that the reduction of the ability to excrete mRNA from blood promoted the delivery of mRNA, that is, the delivery of the drug to various organs.

Example 2: Biokinetics of Polyvalent Cations

In this example, in order to investigate the causes why the above functions were exerted, the biokinetics of the polyvalent cations were clarified.

100 μL of PEGasus-PLL (37×2–20) with a concentration of 12.5 mg/mL fluorescently labeled with Alexa Fluor 594 NHS Ester purchased from Thermo Fisher Scientific Inc. was intravenously injected into a mouse. Then, the blood vessels of the liver were observed with an in-vivo confocal microscope. The accumulation of the polymer in the blood vessels can be evaluated by fluorescence.

Figure 4:
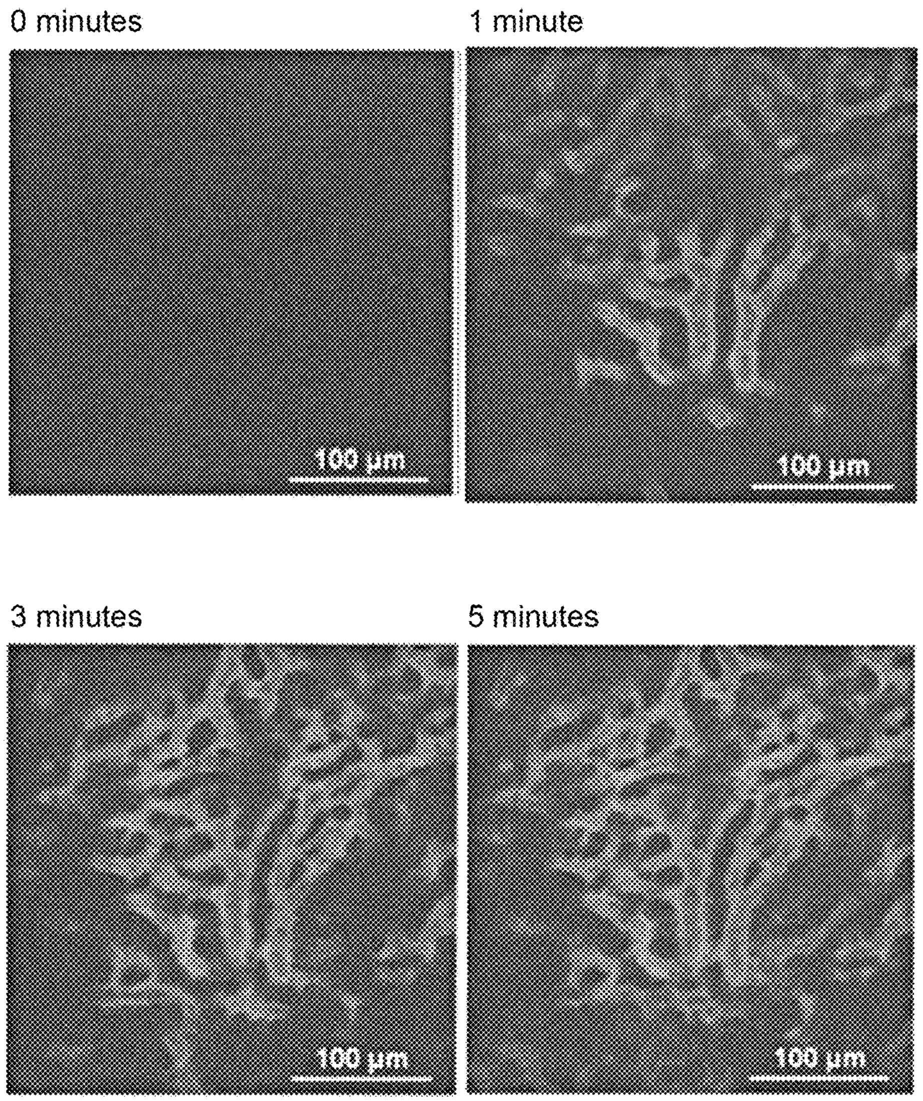
FIG. 4 includes images showing accumulation of polyvalent cations on the inner vascular surface of the liver sinusoidal endothelial cells. In particular, it is shown that the inner surface of the sinusoidal endothelial cells is covered with the polyvalent cations.

The results were as shown in FIG. 4. As shown in FIG. 4, it was observed that the polyvalent cations were adsorbed and accumulated on the inner vascular surface of the sinusoidal endothelial cells 1 minute after the administration.

Figure 5:
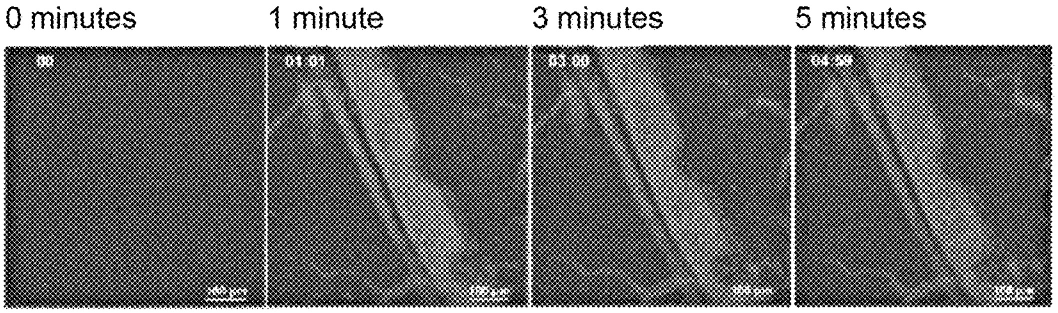
FIG. 5 includes images showing accumulation of polyvalent cations on the inner vascular surface of the peripheral (ear) vascular endothelial cells. In the peripheral vascular endothelial cells, no substantial cover or accumulation of the polyvalent cations is observed.

Next, the ear blood vessels were observed as an example of peripheral blood vessels. As shown in the results in FIG. 5, it could be observed that the polyvalent cations flow in the blood vessels, but accumulation on the inner vascular surface of the ear vascular endothelial cells was not observed.

In this way, the polyvalent cations accumulated on the inner vascular surface of the liver sinusoidal endothelial cells, but accumulation on the inner vascular surface of the peripheral blood vessels was not observed.

In the pharmacokinetics, the liver and kidneys are known to be organs that significantly affect the ability to excrete of drugs from blood. It turned out that the polyvalent cations had the effect of reducing the excretion abilities of the liver sinusoidal endothelial cells and the kidneys from blood and reducing the ability to excrete the drug from blood by adsorbing on the surface of the sinusoidal endothelial cells to physically cover the inner vascular surface. Further, the cover was specific to the liver sinusoidal endothelial cells and the kidney vascular endothelial cells.

Example 3: Effect of Improving Retention of Micelles in Blood by Polyvalent Cations In the aforementioned examples, it was revealed that the polyvalent cations had the effect of reducing the abilities of the liver sinusoidal endothelial cells and the kidneys to excrete the drug from blood.

In this example, it was confirmed that such reduction in the excretion abilities contributed to improvement of retention of the drug in blood.

As the polyvalent cations, 100 μL of a PEGasus-PLL solution adjusted to a concentration of 12.5 mg/mL was intravenously administered to a mouse. 5 minutes later, 200 μL of a polymer micelle solution encapsulating a plasmid DNA (pDNA) created by the method according to Biomaterial, 2017, 126, 31-38 was administered. The pDNA used in this experiment was fluorescently labeled in advance with a Label IT Tracker Cy5 Kit (Mirus Bio LLC). Thereafter, the retention of the pDNA in blood was investigated. The maximum value of the fluorescence intensity was taken as 100%, and the retention of the pDNA in blood was evaluated by the change in fluorescence intensity with the passage of time. As a control group, a group in which 200 μL of the solution adjusted above was intravenously administered without the prior administration of the polyvalent cations to the mouse was also observed.

Figure 6:
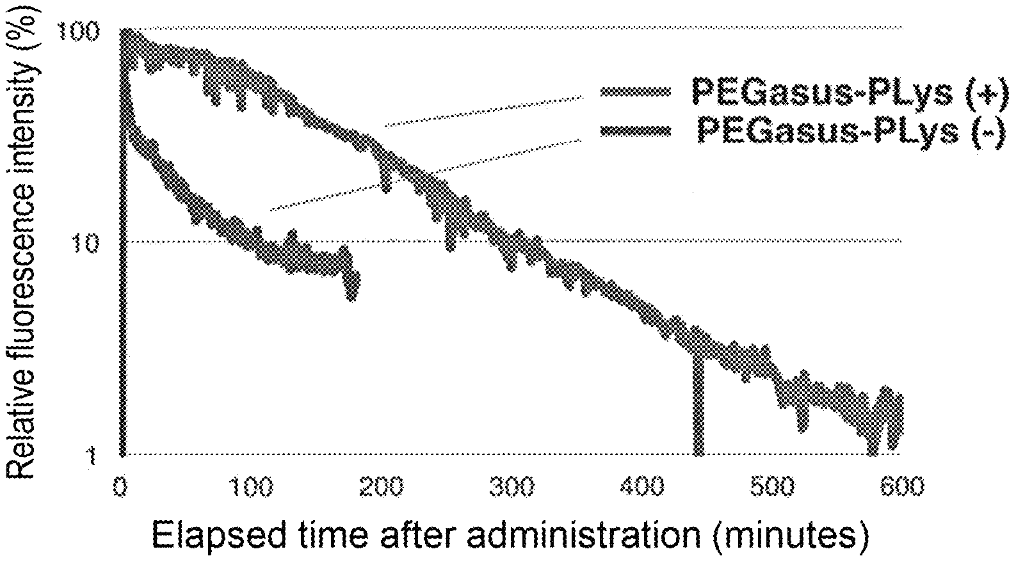
FIG. 6 is a graph showing the effects of a polyvalent cations on retention of a carrier encaspsulating nucleic acids in blood.

The results were as shown in FIG. 6. As shown in FIG. 6, it was demonstrated that the amount of the pDNA remaining in blood rapidly decreased in the group without the prior administration of the polyvalent cations, whereas the retention in blood remarkably increased in the group with the prior administration of the polyvalent cations.

Further, in an experiment using single-stranded PEG, the PEG portion with a larger average molecular weight improved retention in blood (for example, the retention in blood improved more with 60 kD or 70 kD than with 50 kD).

Figure 7:
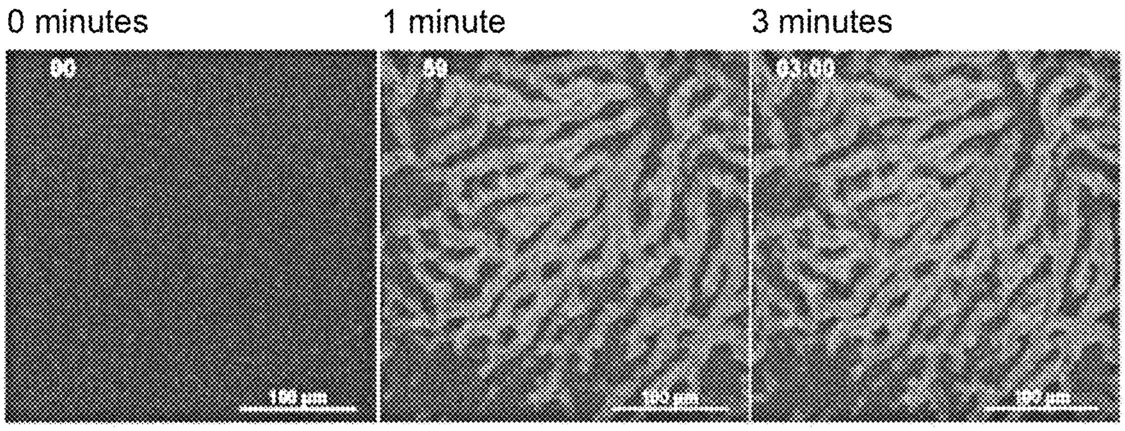
FIG. 7 includes images showing the effects of a polyvalent cations on accumulation of a carrier encapsulating nucleic acids on the inner vascular surface of the liver sinusoidal endothelial cells.
Figure 7:
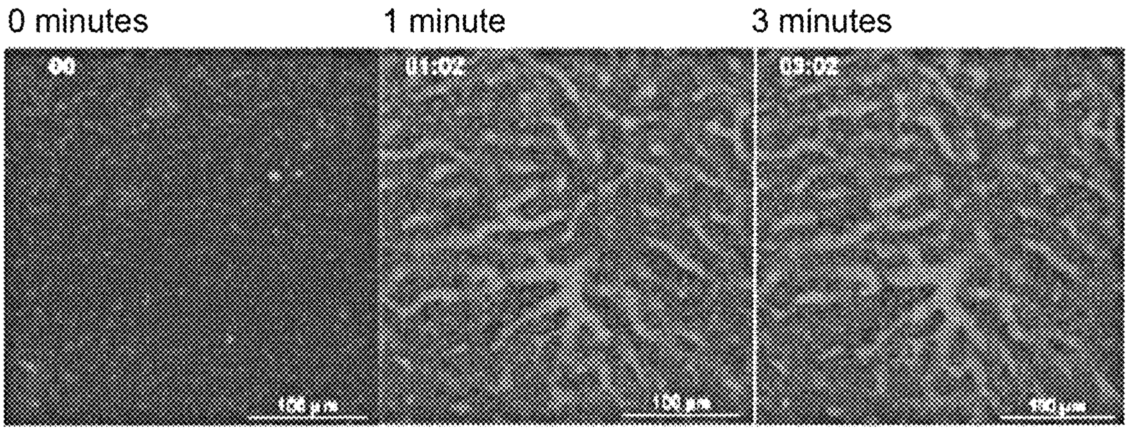

Next, the accumulation of micelles in the liver was observed with an in-vivo confocal microscope. As shown in the upper panel in FIG. 7, it could be observed how the pDNA accumulated on the inner vascular surface of the liver sinusoidal endothelial cells in the group without the prior administration of the polyvalent cations. In contrast, as shown in the lower panel in FIG. 7, the accumulation of the pDNA on the inner vascular surface of the liver sinusoidal endothelial cells remarkably decreased in the group with the prior administration of the polyvalent cations.

It was considered from these results that the ability to excrete the drug from blood was reduced, as observed in Examples 1 and 2, because the inner vascular surface of the liver sinusoidal endothelial cells was covered with the polyvalent cations, thereby inhibiting drug accumulation in the sinusoidal endothelial cells, and the inner vascular surface of the kidney vascular endothelial cells was covered with the cationic polymer, thereby inhibiting excretion of the drug through the glomerulus. Thus, it was considered that, even when administered alone (that is, in a free form), the polyvalent cations had the effect of reducing the ability to excrete the drug from blood to improve the retention in blood and thereby improve the amount of the drug to be delivered to target organs.

Next, the interaction between the polyvalent cations and albumin was investigated. Specifically, the amount of heat generated when albumin and PEGasus-PLL were mixed was measured using a Malvern's isothermal titration calorimeter, Microcal PEAQ-ITC. 200 μL of an albumin solution obtained by dissolving albumin in PBS at a concentration of 33.3 μM was prepared as a cell side sample, and a PEGasus-PLL solution obtained by dissolving PEGasus-PLL in PBS at a concentration of 313 μM was prepared as a syringe side sample. Under stirring at a speed of 750 rpm, 37 μL of the PEGasus-PLL solution was added dropwise to the albumin solution, and the change in heat was observed. As a control experiment, the change in heat when PEGasus-PLL was added dropwise to PBS was observed. As the apparatus conditions, the Filter period was set to 5 seconds, and the Feedback mode was set to high. The results were as shown in FIG. 8.

Figure 8:
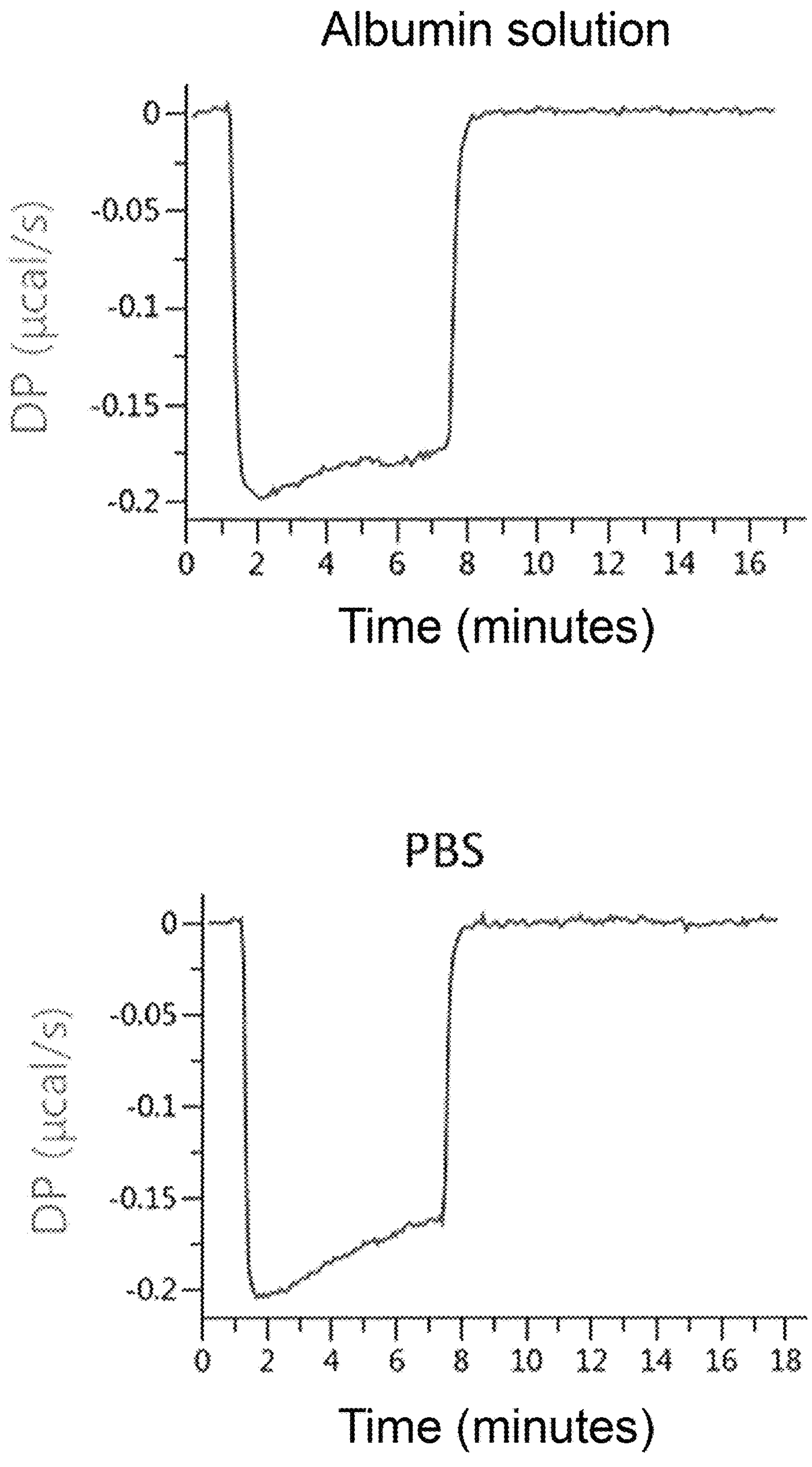
FIG. 8 includes graphs showing that the polyvalent cations of the present invention do not substantially interact with albumin.

As shown in FIG. 8, the change in heat was almost the same in the presence or absence of albumin, and no significant difference was recognized. This result showed that there was no interaction between PEGasus-PLL and albumin, that is, PEGasus-PLL and albumin did not bind to each other. It was considered that PEGasus-PLL improved the retention of the drug in blood due to the effect of reducing the clearance by covering the liver sinusoidal endothelial cells, not due to the effect of excreting the drug by albumin.

Example 4: Improvement of Gene Expression of Lipoplex in Spleen by Polyvalent Cations Invivofectamine (trademark) is commercially available from Invitrogen as a reagent for delivering RNA to the liver. Invivofectamine (trademark) is a reagent for systemic administration of lipid-based mRNA and is said to be particularly suitable for delivering mRNA to the liver.

Here, Invivofectamine (trademark) and mRNA were mixed according to the manufacturer protocol to form a lipid-based mRNA complex (lipoplex).

As the polyvalent cations, 100 μL of a PEGasus-PLL solution adjusted to a concentration of 12.5 mg/mL was intravenously administered to a mouse. 5 minutes later, 200 μL of the invivofectamine solution adjusted above was i.v. administered. 24 hours later, organs (liver and spleen) were extracted. As a negative control group to check the effect of addition of the polymer, comparison with a group in which 200 μL of a solution prepared above was intravenously administered to a mouse without the prior administration of the polyvalent cations was performed. The organs collected were ground with a Lysis buffer (Promega Corporation) and a Multi-Beads Shocker (Yasui Kikai Corporation). The luminescence of luciferase in the suspension was measured with a luminometer (Lumat LB9507, Berthold Technologies GmbH & Co. KG) using a Luciferase assay kit purchased from Promega Corporation according to the manufacturer protocol, to evaluate the gene expression level in the liver and spleen. The results were as shown in FIG. 9.

Figure 9:
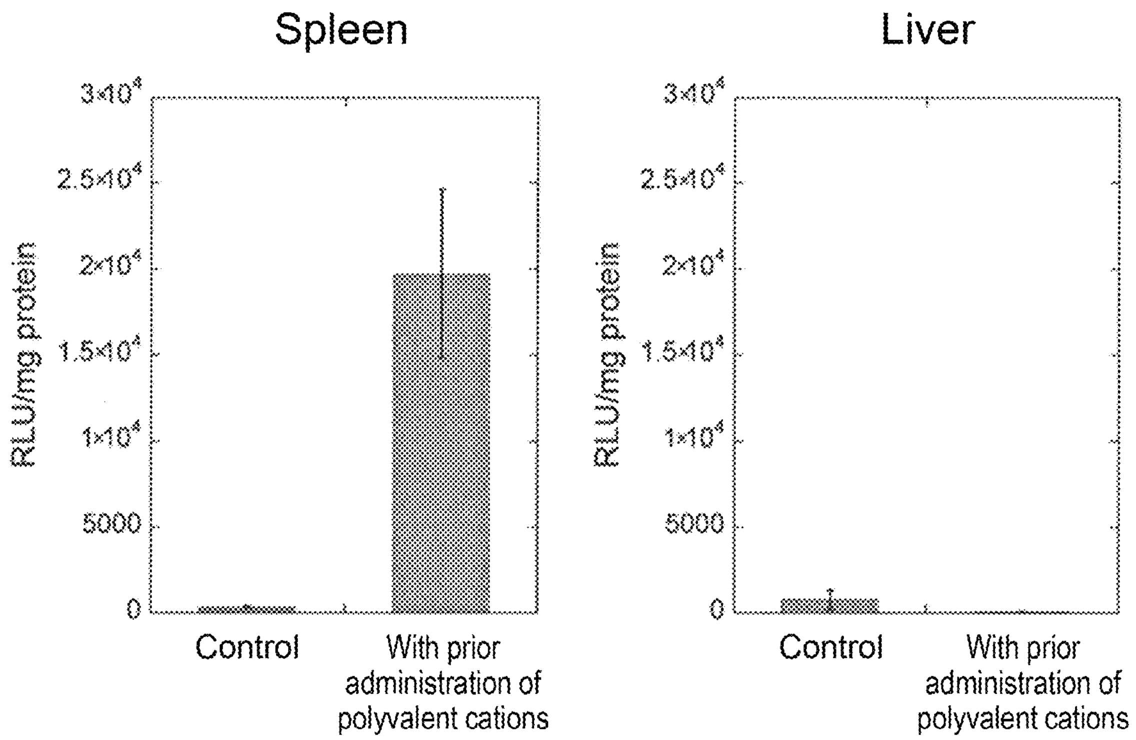
FIG. 9 includes graphs showing the effects of polyvalent cations on accumulation of lipoplex of mRNA in the spleen.

As shown in FIG. 9, addition of the polyvalent cations could enhance the gene expression of Lipoplex in the spleen 100 times or more. In this way, it was proved that the addition of the polyvalent cations suppressed the uptake of the drug into the liver sinusoidal endothelial cells and the endothelial cells of the kidneys and enhanced the retention of the drug in blood, thereby enhancing the accumulation of the drug in organs other than liver and kidneys. FIG. 9 and FIG. 3A are different in that the fluorescence of Cy5 was evaluated in FIG. 3A, whereas the expression level of mRNA administered was evaluated in FIG. 9. These examples revealed that administration of the polyvalent cations was effective for improving the expression level of mRNA in the spleen.

According to the present examples, mRNA can be effectively delivered to the spleen. The spleen is an organ that produces immune cells, and thus the delivery of mRNA to the spleen and the expression thereof are major achievements leading to the development of vaccines such as RNA vaccines and peptide vaccines.

When the polyvalent cations were added, a slight decrease in gene expression in the liver was observed, as in the above examples. This was considered to be attributable to the suppression of the accumulation of lipoplex on the liver sinusoidal endothelium by the previously injected PEGasus-b-PLL. In particular, from the fact that most of the gene expression in the liver was suppressed by PEGasus-b-PLL, it is understood that Lipoplex accumulated mainly in the liver sinusoidal endothelial cells. Meanwhile, since the gene expression of the two in the liver and the difference therebetween was not dramatically significant, it was indicated that high gene expression in the liver could not have been achieved merely by the accumulation of Lipoplex in the liver sinusoidal endothelium. From these results, it was also considered that accumulation of nucleic acids in the liver sinusoidal endothelium contributed to removal of the nucleic acid carrier from blood and also leads to inactivation of the nucleic acids.

Example 5: Excretion Characteristics of bPEG-PLL from Body

In this example, excretion of the polyvalent cations from the body was investigated.

Specifically, bPEG, and bPEG (molecular weight: 40 k×2)-PLL (TFA) (polymerization degree: 20) and PEG (molecular weight: 80 k)-PLL (TFA) (polymerization degree: 20), which were synthesized by polymerizing Lys (TFA)-NCA as above, were fluorescently labeled using Alexa Fluor 594 NHS ester purchased from Thermo Fisher Scientific Inc. The bPEG-PLL (TFA) and PEG-PLL (TFA) were fluorescently labeled into bPEG-PLL and PEG-PLL by deprotecting the TFA protecting group with a base, as described above. 100 μL each of solutions of these adjusted to a concentration of 12.5 mg/mL was intravenously administered to the tail of a mouse, and the retention in blood was observed with an in-vivo confocal microscope. The results were as shown in FIG. 10.

For bPEG-PLL, the luminal inner wall of the liver sinusoidal endothelial cells was observed with an in-vivo confocal microscope. The results were as shown in FIG. 11.

Figure 10:
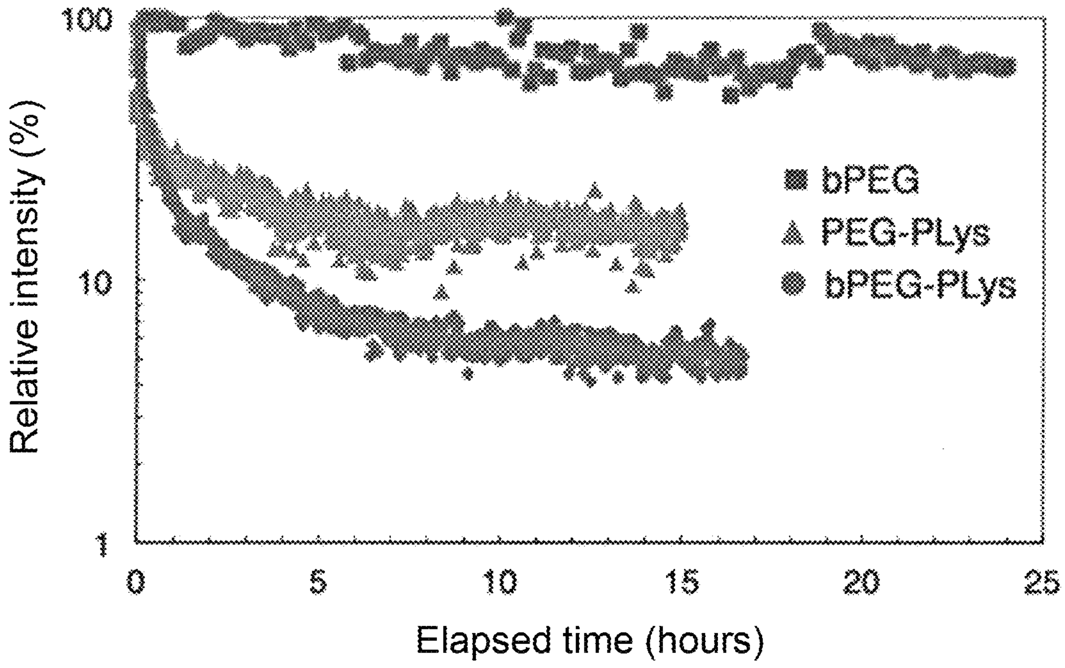
FIG. 10 is a graph showing retention of bPEG-PLL, PEG-PLL, and bPEG in blood.

As shown in FIG. 10, bPEG-PLL and PEG-PLL to which lysine as the polyvalent cations with a polymerization degree of 20 was bound exhibited low retention in blood as compared with bPEG having no cationic blocks. In particular, the bPEG-PLL was almost excreted from blood 10 hours later (FIG. 10). From this fact, it was suggested that the cationic block had an effect of reducing the retention of bPEG in blood.

Figure 11:
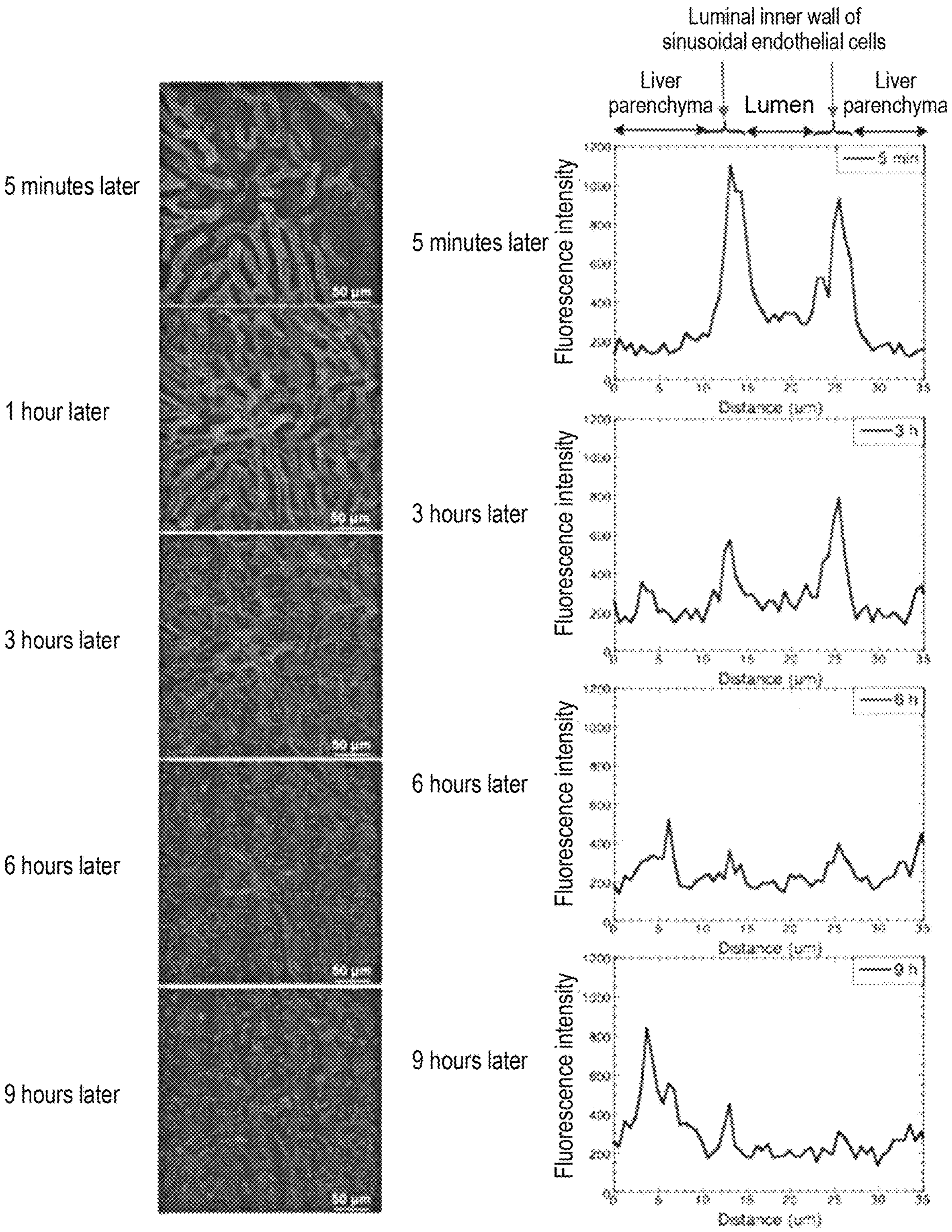
FIG. 11 includes images and graphs showing time course of the amount of bPEG-PLL on the luminal inner wall of the liver sinusoidal endothelial cells.

Further, as shown in FIG. 11, the abundance of bPEG-PLL covering the luminal inner wall of the sinusoidal endothelial cells was observed over time. As a result, the cover on the inner wall could continuously exist for at least 1 hour or more after the administration but almost disappeared from the inner wall 6 hours after the administration (FIG. 11).

It was considered from this that bPEG-PLL covered the luminal inner wall of the endothelial cells by being administered alone in a free form to reduce the drug clearance for a sufficient time to deliver the drug but could disappear after the completion of the delivery of the drug. It was further suggested from the experiment using bPEG-PLL that the polyvalent cations of the present invention could be administered in a single dose or multiple doses along with the timing of the administration of the drug (or before or after that) so as to reduce the clearance of the drug administered for a required time. Further, it was suggested from the experiment using bPEG-PLL that the polyvalent cations of the present invention could be administered by a method (frequency and dose or the like) so as to be excreted from the body after the completion of the delivery of the drug.

Example 6: Delivery Experiment Using Virus Particles

In this example, the influence of administration of the polyvalent cations on gene delivery by virus particles was investigated.

PEGasus-b-PLL was used as the polyvalent cations. Further, adeno-associated virus (AAV8) was used as the virus particles. AAV8 into which genes encoding firefly luciferase were incorporated under the CMV promoter was purchased from Vector Biolabs (Catalog #: VB1473). AAV8 ($1 \times 10^{10}$ viral genomes/mouse) was administered through the tail vein of a mouse (Balb/c, female, 6 week-old). 21 days after the administration, the tissue of each organ (liver, pancreas, quadriceps, and thigh) was collected at the sacrifice of the mouse, and 100 mg of the tissue was homogenized in 1 mL of a passive lysis buffer. The homogenate was centrifuged at 18,000 g and 4° C. for 10 minutes, and luminescence was detected by luciferase in 20 μL of the supernatant. BCA assay was performed to determine the protein concentration. The luciferase activity was expressed in relative light unit (RLU) normalized to the protein content. The results were as shown in FIG. 12.

Figure 12:
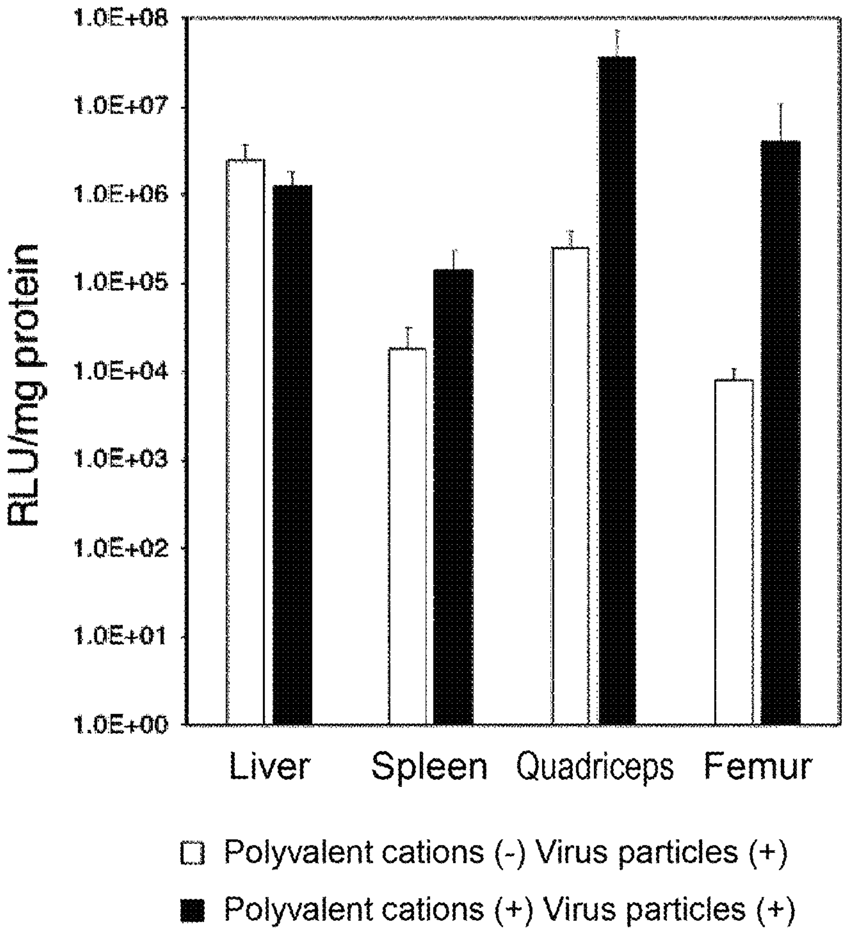
FIG. 12 is a graph showing the influence of polyvalent cations on accumulation potential of virus particles in each organ.

As shown in FIG. 12, the polyvalent cations reduced the luciferase introduction efficiency into the liver by AAV8 and enhanced the expression of luciferase in the tissues of the pancreas, quadriceps, and thigh. It was assumed that the accumulation potential in the liver was reduced, and the accumulation in multiple organs was increased. It was confirmed from this that the effects of changing the kinetics of the drug to be administered and reducing the clearance by the polycations of the present invention were also exerted on the virus particles.

Figure 13:
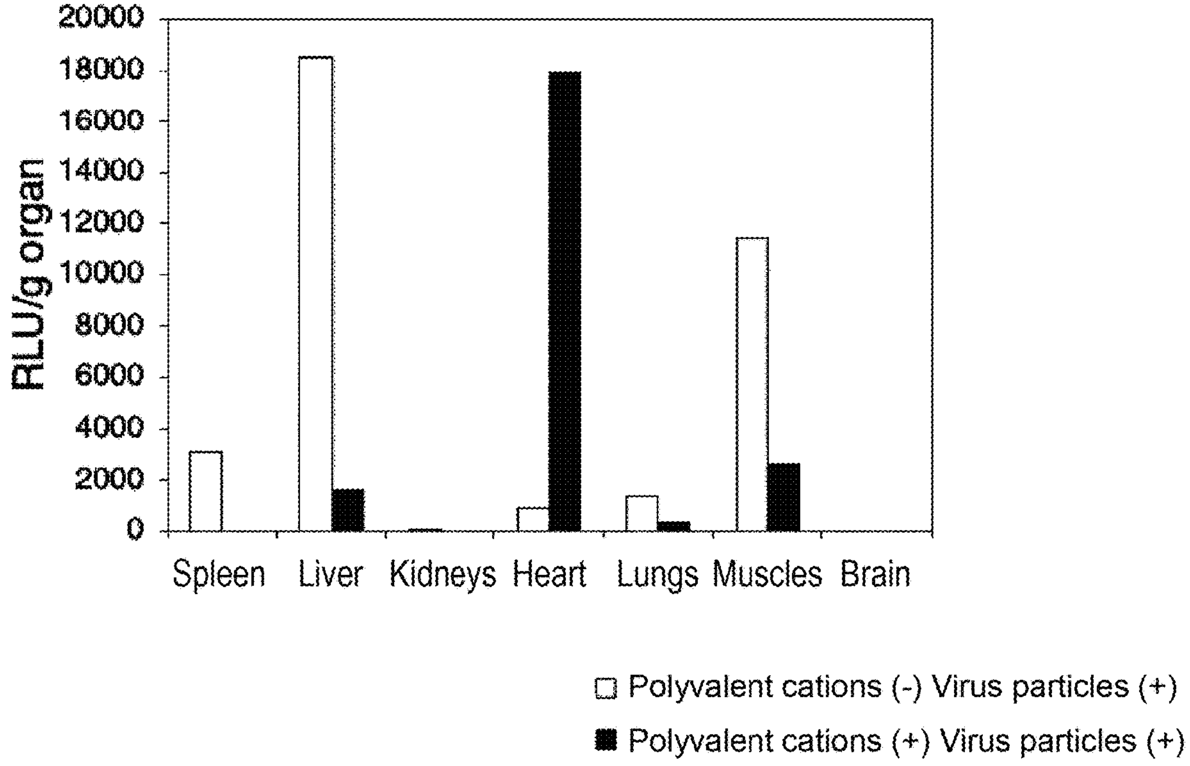
FIG. 13 is a graph showing the influence of polyvalent cations on accumulation potential of virus particles in each organ.

Next, the same experiment as above was performed except that AAV9 capable of delivering genes to the heart muscle was used instead of AAV8. AAV9 into which genes encoding firefly luciferase were incorporated under the CMV promoter was purchased from SignaGen Laboratories (Catalog #: SL101494). However, the dose was set to $5 \times 10^{10}$ viral genomes/mouse, and the mouse was sacrificed 2 days after the administration. As a result, the polyvalent cations enhanced the accumulation of AAV9 in the heart and enhanced the gene transfer efficiency into the heart, while reducing the accumulation potential in the liver and reducing the gene transfer efficiency into the liver, as shown in FIG. 13.

In this way, it was demonstrated that, although the virus tissue specificity differed depending on the virus type and serotype, the cationic polymer (polycations) according to the present invention would reduce the clearance of not only micelles but also particulate materials such as virus particles in the liver by blocking the surface of the liver sinusoidal endothelial cells, to enhance the organ or tissue specificity of the virus itself as a result of above or at the same time.

The invention claimed is:

1. A composition comprising a first polyvalent cation and a carrier encapsulating a drug, wherein the carrier is at least one selected from the group consisting of a virus, a liposome, and a micelle, wherein when the carrier comprises a second polyvalent cation, the second polyvalent cation is different from the first polyvalent cation, wherein the first polyvalent cation comprises a cationic polymer block and a polyethylene glycol (PEG) block, wherein the PEG block comprises a branched PEG that is branched at one site, has PEG chains extending from the branched site, and has a total average molecular weight of from 40 k Da to 100 k Da, and each PEG chain extending from the branched site independently has an average molecular weight of from 20 k Da to 60 k Da;

wherein the cationic polymer block has an average polymerization degree of from 15 to 80, and has at least one cationic natural amino acid selected from the group consisting of histidine, tryptophan, ornithine, arginine and lysine, and cationic non-natural amino acid selected from the group consisting of aspartate and glutamate modified with a side chain shown by $-(NH-(CH_2)_2)_p-NH_2$, where p represents an integer of 1 to 5; and wherein the first polyvalent cation reduces clearance function of endothelial cells of liver sinusoidal endothelial cells and/or kidney vascular endothelial cells in a body received the composition.

2. The composition according to claim 1, wherein the first polyvalent cation is in a free form and does not bind to the carrier and the drug.

3. The composition according to claim 1, wherein the carrier comprises a triblock copolymer comprising a hydrophilic block, a temperature responsive block, and a cationic block.

4. The composition according to claim 1, wherein the carrier is a virus vector that comprises an expression unit comprising a nucleic acid operably linked to a promoter or enhancer to express the nucleic acid in cells.

5. The composition according to claim 1, wherein the first polyvalent cation in a free form is a cationic polymer having two or more hydrophilic polymer chains, and wherein the polyvalent cation in the carrier comprises a polyvalent cation having a single hydrophilic polymer chain.

6. The composition according to claim 1, wherein the virus is selected from the group of retrovirus vector, lentiviral vector, adenoviral vector, and adeno-associated viral vector.

7. The composition according to claim 1, wherein the carrier is a liposome.

8. The composition according to claim 1, wherein the drug is a nucleic acid, wherein the carrier comprises the nucleic acid and a polyvalent cation that is different from the polyvalent cation in a free form and binds to the nucleic acid.

9. The composition according to claim 1, wherein the drug is a nucleic acid, and wherein the carrier comprises a triblock polyvalent cation that is different from the first polyvalent cation in a free form, and wherein the triblock polyvalent cation comprises a polyethylene glycol block (PEG block), a temperature-responsive block, and a cationic block.

10. The composition according to claim 1, wherein the drug is a nucleic acid, and wherein the carrier is a virus vector that comprises an expression unit comprising a nucleic acid operably linked to a promoter or enhancer to express the nucleic acid in cells.

11. The composition according to claim 1, wherein the virus is selected from the group of retrovirus vector, lentiviral vector, adenoviral vector, and adeno-associated viral vector.

12. The composition according to claim 1, wherein the drug is a nucleic acid, and wherein the carrier is a liposome.

13. The composition according to claim 1, wherein the first polyvalent cation has two or more hydrophilic polymer chains.

14. The composition according to claim 1, wherein the first polyvalent cation has two or more hydrophilic polymer chains.

15. A combination, comprising (i) a composition comprising a first polyvalent cation and (ii) a composition comprising a carrier encapsulating a drug, wherein the carrier is at least one selected from the group consisting of a virus, a liposome, and a micelle, wherein when the carrier comprises a second polyvalent cation, the second polyvalent cation is different from the first polyvalent cation, wherein the first polyvalent cation comprises a cationic polymer block and a polyethylene glycol (PEG) block, wherein the PEG block comprises a branched PEG that is branched at one site, has PEG chains extending from the branched site, and has a total average molecular weight of from 40 k Da to 100 k Da, and each PEG chain extending from the branched site independently has an average molecular weight of from 20 k Da to 60 k Da;

wherein the cationic polymer block has an average polymerization degree of from 15 to 80, and has at least one cationic natural amino acid selected from the group consisting of histidine, tryptophan, ornithine, arginine, lysine, and a cationic non-natural amino acid selected from the group consisting of aspartate and glutamate modified with a side chain shown by $-(NH-(CH_2)_2)_p-NH_2$, where p represents an integer of 1 to 5; and wherein the first polyvalent cation reduces clearance function of endothelial cells of liver sinusoidal endothelial cells and/or kidney vascular endothelial cells in a body received the composition.

16. The combination according to claim 15, wherein the first polyvalent cation is in a free form and does not bind to the carrier and the drug.

17. The combination according to claim 15, wherein the carrier comprises a triblock copolymer comprising a hydrophilic block, a temperature responsive block, and a cationic block.

18. The combination according to claim 15, wherein the carrier is a virus vector that comprises an expression unit comprising a nucleic acid operably linked to a promoter or enhancer to express the nucleic acid in cells.

19. The combination according to claim 15, wherein the first polyvalent cation in a free form is a cationic polymer having two or more hydrophilic polymer chains, and wherein the polyvalent cation in the carrier comprises a polyvalent cation having a single hydrophilic polymer chain.

20. The combination according to claim 15, wherein the virus is selected from the group of retrovirus vector, lentiviral vector, adenoviral vector, and adeno-associated viral vector.

21. The combination according to claim 15, wherein the carrier is a liposome.

22. The combination according to claim 15, wherein the drug is a nucleic acid, wherein the carrier comprises the nucleic acid and a polyvalent cation that is different from the polyvalent cation in a free form and binds to the nucleic acid.

23. The combination according to claim 15, wherein the drug is a nucleic acid, and wherein the carrier comprises a triblock polyvalent cation that is different from the first polyvalent cation in a free form, and wherein the triblock polyvalent cation comprises a polyethylene glycol block (PEG block), a temperature-responsive block, and a cationic block.

24. The combination according to claim 15, wherein the drug is a nucleic acid, and wherein the carrier is a virus vector that comprises an expression unit comprising a nucleic acid operably linked to a promoter or enhancer to express the nucleic acid in cells.

25. The combination according to claim 15, wherein the virus is selected from the group of retrovirus vector, lentiviral vector, adenoviral vector, and adeno-associated viral vector.

26. The combination according to claim 15, wherein the drug is a nucleic acid, and wherein the carrier is a liposome.

27. The combination according to claim 15, wherein the first polyvalent cation has two or more hydrophilic polymer chains.

28. The combination according to claim 15, wherein the first polyvalent cation has two or more hydrophilic polymer chains.

* * * * *